(12) United States Patent
Ryu et al.

(10) Patent No.: US 8,278,263 B2
(45) Date of Patent: Oct. 2, 2012

(54) METHOD OF REGULATING MAMMALIAN TARGET-OF-RAPAMYCIN ACTIVITY BY INTERACTION BETWEEN PHOSPHOLIPASE D AND RAPTOR

(75) Inventors: Sung-Ho Ryu, Pohang (KR);
Pann-Ghill Suh, Pohang (KR);
Sang-Hoon Ha, Pohang (KR);
Do-Hyung Kim, Minneapolis, MN (US);
Il-Shin Kim, Pohang (KR); Jung-Hwan Kim, Pohang (KR); Mi-Nam Lee, Pohang (KR); Hyun-Ju Lee, Pohang (KR); Jong Heon Kim, Goyang (KR); Sung-Key Jang, Pohang (KR);
Tae-Hoon Lee, Pohang (KR)

(73) Assignee: Postech Academy-Industry Foundation, Pohang (KR)

( * ) Notice: Subject to any disclaimer, the term of this patent is extended or adjusted under 35 U.S.C. 154(b) by 791 days.

(21) Appl. No.: 12/374,262

(22) PCT Filed: Aug. 3, 2007

(86) PCT No.: PCT/KR2007/003753
§ 371 (c)(1),
(2), (4) Date: Jan. 16, 2009

(87) PCT Pub. No.: WO2008/016281
PCT Pub. Date: Feb. 7, 2008

(65) Prior Publication Data
US 2010/0184636 A1 Jul. 22, 2010

Related U.S. Application Data

(60) Provisional application No. 60/821,535, filed on Aug. 4, 2006.

(51) Int. Cl.
*A61K 38/02* (2006.01)
(52) U.S. Cl. .............................. 514/1.1; 435/29; 530/300
(58) Field of Classification Search ........................ None
See application file for complete search history.

(56) References Cited

FOREIGN PATENT DOCUMENTS
WO WO-2004/026898 4/2004
WO WO 2004/026898 * 4/2004

OTHER PUBLICATIONS

Ha et al., Cellular Signaling, Jun. 2006, pp. 2284-2290.*
Ha et al., Cellular Signaling, 2006, pp. 2284-2290.*
International Search Report and Written Opinion for PCT/KR2007/003753 dated Nov. 13, 2007.
Ha et al., "PLD2 forms a functional complex with mTOR/raptor to transduce mitogenic signals," *Cellular Signalling*, 18:2283-2291 (2006).
Hay et al., "Upstream and downstream of mTOR," *Genes Dev.*, 18:1926-1945 (2004).
Hornberger et al., "The role of phospholipase D and phosphatidic acid in the mechanical activation of mTOR signaling in skeletal muscle," *PNAS*, 103:4741-4746 (2006).

* cited by examiner

*Primary Examiner* — Christopher R. Tate
*Assistant Examiner* — Roy Teller
(74) *Attorney, Agent, or Firm* — Marshall, Gerstein & Borun LLP

(57) ABSTRACT

The present invention relates to a method of regulating mammalian target-of-rapamycin (mTOR) by regulating a phospholipase D (PLD) activity that generates a complex with mTOR. Further, the present invention also relates to a method of screening inhibitors of mTOR, and a method and a composition for treating mTOR-related metabolic diseases by inhibiting mTOR.

2 Claims, 14 Drawing Sheets

METHOD OF REGULATING MAMMALIAN TARGET-OF-RAPAMYCIN ACTIVITY BY INTERACTION BETWEEN PHOSPHOLIPASE D AND RAPTOR

CROSS REFERENCE TO RELATED APPLICATION

This application claims priority to and the benefit of Provisional Application No. 60/821,535 filed on Aug. 4, 2006, which is hereby incorporated by reference for all purposes as if fully set forth herein.

BACKGROUND OF THE INVENTION (a) Field of the Invention

The present invention relates to a method of regulating mammalian target-of-rapamycin (mTOR) by regulating a phospholipase D (PLD) activity that generates a complex with mTOR. Further, the present invention also relates to a method of screening inhibitors of mTOR, and a method and a composition for treating mTOR-related metabolic diseases by inhibiting mTOR.

(b) Description of the Related Art mTOR is a serine/threonine protein kinase and a member of a novel superfamily of signaling proteins termed PI 3-kinase related kinases (PIKKs), based on sequence similarity of their catalytic domains. The mTOR pathway is an emerging target for the treatment of cancer, diabetes and obesity. Further, recent studies have demonstrated the mTOR's role as a mediator of lifespan control in *C. elegans* and *Drosophila*. However, despite the significance of this pathway in such diverse biological processes, the mechanism of its regulation by upstream signals remains to be addressed.

In addition, mTOR requires the lipid second messenger phosphatidic acid (PA) for its activation. PA is an enzymatic product of PLD. PLD, which hydrolyzes phosphatidylcholine (PC) to generate PA, constitutes another branch of the mTOR upstream regulators through which mitogenic signals impinge on the mTOR pathway. Mammalian PLD isozymes identified to date, PLD1 and PLD2, sense a variety of signals, such as neurotransmitters, hormones and growth factors, to regulate multiple physiological events such as proliferation, secretion, respiratory burst and actin cytoskeletal reorganization, and the like.

Here, the present inventors have studied regarding the regulatory mechanisms of mTOR signaling and found that the physical/functional connections between mitogen-induced PA generation and its effector, mTOR, to complete the present invention (see FIG. 21).

SUMMARY OF THE INVENTION

An aspect of the present invention is to reveal a functional/physical relationship between PLD, raptor and mTOR, and a mechanism of forming a PLD/raptor/mTOR complex to activating the mTOR activity.

Based on the above, another aspect of the present invention is to provide a method of regulating mTOR activity by regulating interactions between PLD and raptor thereby regulating formation of a complex of PLD and mTOR through raptor. The regulating method may be comprise the step of inhibiting interactions between PLD and raptor, thereby inhibiting formation of a complex of PLD and mTOR through raptor, to inhibit mTOR activity.

Another aspect of the present invention is to provide a method of screening inhibitors of mTOR activity. The method of screening inhibitors of mTOR according to the present invention may comprising the steps of:
contacting a candidate compound to a sample cell;
examining the interaction between PLD and mTOR through raptor to form a complex; and
determining the compound as an inhibitor of mTOR activity when the level of the interaction between PLD and mTOR decreases compared with that in other sample cells without contacting with the compound.

Another aspect of the present invention is to provide the amino acid sequence of SEQ ID NO: 4 as a target for screening of an agent of treating mTOR-related metabolic diseases may include cancer, diabetes, obesity, hamartoma syndrome including tuberous sclerosis complex, Peutz-Jeghers syndrome, Cowden disease, tissue/organ hypertrophy including cardiac hypertrophy, etc.

Still other aspect of the present invention is to provide methods and compositions for treating mTOR-related metabolic diseases by inhibiting mTOR activity, more specifically, by inhibiting the interaction between PLD2 and raptor, thereby inhibiting the formation of a complex of PLD2 and mTOR through raptor (PLD/raptor/mTOR complex). The mTOR-related metabolic diseases may include cancer, diabetes, obesity, hamartoma syndrome including tuberous sclerosis complex, Peutz-Jeghers syndrome, Cowden disease, tissue/organ hypertrophy including cardiac hypertrophy, etc.

DETAILED DESCRIPTION OF THE PREFERRED EMBODIMENTS

A more complete appreciation of the invention, and many of the attendant advantages thereof, will be readily apparent as the same becomes better understood by reference to the following detailed description.

The present inventor found that PLD2 is identified as a novel raptor binding partner, suggesting that PLD2 is an important molecular link in mitogen-regulated mTOR signaling, and that it presents a novel regulatory point that can be targeted for the treatment of metabolic diseases, to complete the present invention.

The present inventors have been studied the regulatory mechanisms of mTOR signaling, and found the participation of the mTOR complex (mTOR/raptor) containing raptor and GβL in response to upstream signals for the appropriate control of cell growth and the other mTOR complex (mTOR/rictor) containing rictor and GβL for the control of actin cytoskeletone (Kim, D. H., Sarbassov, D. D., Ali, S. M., Latek, R. R., Guntur, K. V., Erdjument-Bromage, H., Tempst, P., Sabatini, D. M. Mol. Cell 11 (2003) 895, which is hereby incorporated by reference). The upstream signals may be derived from insulin, nutrients, and/or mitogens. The present invention has been completed by finding the physical connection as well as the functional connection between mTOR complex and the upstream regulators.

Further, in the present invention, it was studied that which isozyme is mainly involved in mitogen-induced mTOR activation, revealing that PLD2 is a major isozyme to transduce mitogenic signaling to mTOR/raptor and the activity of mTOR is achieved by complex formation between PLD2 and mTOR/raptor. As a result, the present invention suggests the physical/functional connections between mitogen-induced PA generation and its effector mTOR and would provide further insight into mTOR-related metabolic diseases such as cancer, diabetes and obesity.

Figure 21:
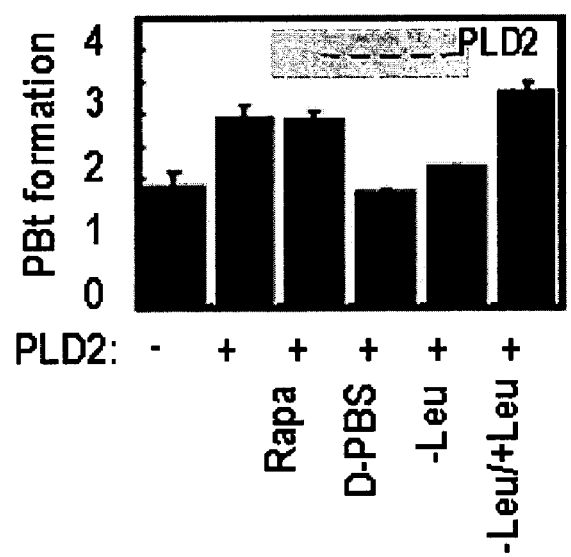
FIG. 21 shows the level of PBt formation in presence or absence of leucine.

The present invention suggests that PLD2 might function as a mediator of mitogen-induced mTOR activation. Further, in the present invention, it is found that PLD2 binds to raptor through its TOS motif-like sequence (FIG. 21), and that the mitogen-induced PLD2-raptor interaction allows PA accumulation near mTOR, enabling PA-dependent mTOR activation, resulting phosphorylation of mTOR effectors, such as S6K1, 4EBP1, and the like.

DEFINITION

The term 'mTOR' refers to a mammalian target-of-rapamycin. In the present invention, mTOR may be originated from any mammalians including human and its amino acid sequences according to the source species are well known in the relevant art. In the present invention, the mTOR may originated from any mammalians, for example, *Homo sapiens* (NP 004949), *Drosophila melanogaster* (NP524891), *Caenorhabditis elegans* (Q95Q95), etc. In an embodiment of the present invention, human mTOR having the amino acid sequence of SEQ ID NO: 1 may be used.

The term 'PLD' refers to a phospholipase D, and mammalian PLD isozymes include to classes, PLD1 and PLD2. In the present invention, PLD may be originated from any mammalians including human, and its amino acid sequences according to the source species are well known in the relevant art. In an embodiment of the present invention, PLD1 (e.g., NM 030992 originated from *Rattus norvegicus*) having the amino acid sequence of SEQ ID NO: 2 and PLD2 (e.g., NM 002663 originated from *Homo sapiens*) having the amino acid sequence of SEQ ID NO: 3 may be used.

The term 'PA' refers to a phosphatidic acid, which is an enzymatic product of PLD. mTOR requires the lipid second messenger phosphatidic acid (PA) for its activation.

The term 'TOR signal (TOS) motif-like sequence' refers to an amino acid sequence of upstream or downstream regulators of mTOR, which actually functions to bind to raptor. In an embodiment of the present invention, the TOS motif-like sequence of PLD2 may have the amino acid sequence of SEQ ID NO: 4.

The term 'raptor' refers to a regulatory-associated protein of mTOR. In the present invention, the raptor may be originated from any mammalians including human and its amino acid sequences according to the source species are well known in the relevant art. In an embodiment of the present invention, the raptor may be originated from human, and have the amino acid sequence of SEQ ID NO: 5 (Accession No. Q8N122).

An aspect of the present invention is to reveal a functional/physical relationship between PLD, raptor and mTOR, and a mechanism of forming a PLD/raptor/mTOR complex to activating the mTOR activity.

Based on the above, another aspect of the present invention is to provide a method of regulating mTOR activity by regulating interactions between PLD and raptor thereby regulating formation of a complex of PLD and mTOR through raptor. The regulating method may be comprise the step of inhibiting interactions between PLD and raptor, thereby inhibiting formation of a complex of PLD and mTOR through raptor, to inhibit mTOR activity.

Figure 24:
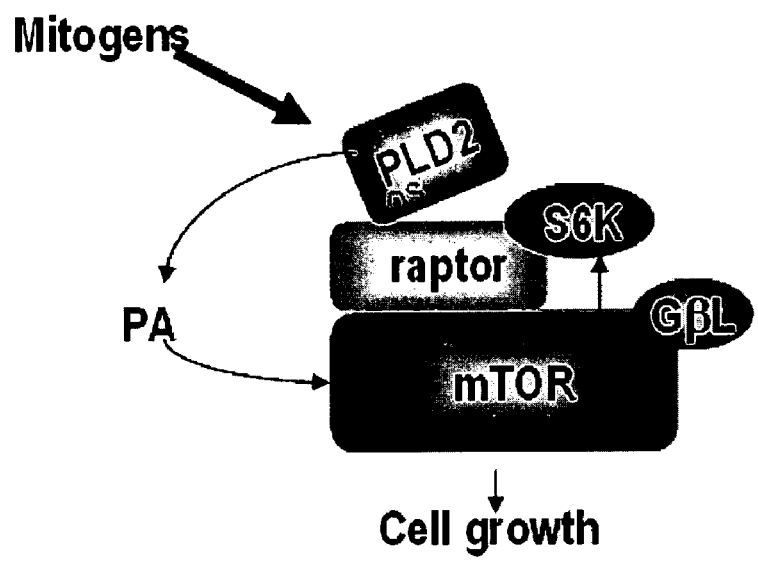
FIG. 24 is a schematic view of PLD2/raptor/mTOR complex.

More specifically, the present invention provides a method of inhibiting mTOR by inhibiting the interaction between PLD and raptor, thereby inhibiting formation of a complex of PLD and mTOR through raptor (PLD/raptor/mTOR complex, FIG. 24). The inhibition of the formation of the PLD/raptor/mTOR complex may be conducted by inactivating a binding domain of PLD, especially PLD2, capable of binding to raptor (raptor binding domain of PLD or PLD2), or a binding domain of raptor capable of binding to PLD, especially PLD2 (PLD- or PLD2 binding domain of raptor). The raptor binding domain of PLD may comprise a TOR signal (TOS) motif-like sequence. In a preferable embodiment, the PLD may be a PLD2, and the raptor binding domain of PLD2 may be a polypeptide consisting of 50 to 200 amino acids, more preferably 100 to 180 amino acids, and essentially comprising PH domain of PDL2, more preferably the amino acid sequence of FEVQV (SEQ ID NO: 4) that is one of TOS motif-like sequence. In an embodiment, the raptor binding domain of PLD2 comprises the amino acid residues from the 186 position to the 308 position in the full-length amino acid sequence of PLD2 (SEQ ID NO: 2).

The inactivation of the raptor binding domain of PLD may be conducted by modifying the amino acid sequence of the raptor binding domain. For example, the modification of the raptor binding domain of PLD may be deletion of one or more amino acids located in the TOS motif-like sequence, preferably one or more amino acids located in the amino acid sequence of SEQ ID NO: 4. Alternatively, the modification of the raptor binding domain of PLD may be substitution of one or more amino acids located in the TOS motif-like sequence, preferably one or more amino acids located in the amino acid sequence of SEQ ID NO: 4, with other amino acid(s), preferably selected from the group consisting of alanine, isoleucine, leucine, methionine, phenylalanine, proline, tryptophan, valine, asparagine, cysteine, glutamine, glycine, serine, threonine, tyrosine, aspartic acid, glutamic acid, arginine, histidine, and lysine. Alternatively, the modification of the raptor binding domain of PLD may be addition of one or more amino acids, preferably selected from the group consisting of alanine, isoleucine, leucine, methionine, phenylalanine, proline, tryptophan, valine, asparagine, cysteine, glutamine, glycine, serine, threonine, tyrosine, aspartic acid, glutamic acid, arginine, histidine, and lysine, to the TOS motif-like sequence, preferably the amino acid sequence of SEQ ID NO: 4.

The PLD binding domain of raptor may comprise the amino acid residues from the 1020 position to the 1335 position in the full-length amino acid sequence of raptor (SEQ ID NO: 5). The inactivation of the PLD binding domain of raptor may be conducted by deleting the polypeptide fragment consisting essentially of the amino acid sequence of the raptor binding domain.

Alternatively, the inactivation of the raptor binding domain of PLD may be conducted by change of pH or temperature of the raptor binding domain of PLD2 or the PLD2 binding domain of raptor, and the like.

The interaction between PLD2 and raptor may be regulated by nutrient levels, preferably amino acid level, more preferably leucine level, such that this interaction is stabilized under high nutrient conditions and weakened under low nutrient conditions. Therefore, the interaction between PLD2 and raptor may be inhibited by decreasing the level of nutrients, preferably amino acids, more preferably leucine.

The method of inhibiting mTOR according to the present invention results in inhibiting the mTOR' phosphorylation activity on one or more mTOR effectors selected from the group consisting of ribosomal protein S6 kinase 1 (S6K1; e.g., NP 003152, NP 082535, etc.), and 4E-binding protein-1 (4EBP1; e.g., NP 004086).

Another aspect of the present invention is to provide a method of screening inhibitors of mTOR activity. The method of screening inhibitors of mTOR according to the present invention may comprise the steps of:

contacting a candidate compound to a sample cell;

examining the interaction between PLD and mTOR through raptor to form a complex; and determining the compound as an inhibitor of mTOR activity when the level of the interaction between PLD and mTOR decreases compared with that in other sample cells without contacting with the compound.

The sample cell may be any cell capable of expressing PLD, more preferably PLD2. For example, the sample cell may be selected from the group consisting of a human embryonic kidney (HEK293), a human epithelial ovarian cancer cell (OVCAR-3), COS7 cell, a human cervical cancer (HeLa) cell, a human colon cancer cell (PC-3), a human breast cancer cell (MB231), a human hepatoma (HepG2), a human breast cancer cell (MCF-7), a human T cell leukemia (Jurkat), and the like. The inhibitor of mTOR may be useful in treating mTOR-related metabolic diseases, such as cancer, diabetes, obesity, hamartoma syndrome including tuberous sclerosis complex, Peutz-Jeghers syndrome, Cowden disease, tissue/organ hypertrophy including cardiac hypertrophy, etc. Therefore, the method of the present invention may also used in screening agents of mTOR-related metabolic disease selected from the group consisting of cancer, diabetes, obesity, hamartoma syndrome including tuberous sclerosis complex, Peutz-Jeghers syndrome, Cowden disease, tissue/organ hypertrophy including cardiac hypertrophy, etc.

The interaction between PLD and mTOR through raptor may be examined by any conventional method, for example immunoprecipitation, but not limited thereto.

Another aspect of the present invention is to provide the amino acid sequence of SEQ ID NO: 4 as a target for screening of an agent of treating mTOR-related metabolic diseases may include cancer, diabetes, obesity, hamartoma syndrome including tuberous sclerosis complex, Peutz-Jeghers syndrome, Cowden disease, tissue/organ hypertrophy including cardiac hypertrophy, etc.

Still other aspect of the present invention is to provide methods and compositions for treating mTOR-related metabolic diseases by inhibiting mTOR activity, more specifically, by inhibiting the interaction between PLD2 and raptor, thereby inhibiting the formation of a complex of PLD2 and mTOR through raptor (PLD/raptor/mTOR complex). The treating method may comprise the step of inactivating the raptor binding domain of PLD, thereby inhibiting formation of a complex of PLD and mTOR through raptor. The inactivation of the raptor binding domain of PLD is as aforementioned. Alternatively, the treating method comprises the step of administering an effective amount of an inhibitor of mTOR as an active ingredient, wherein the inhibitor of mTOR may be screened by the screening method according to the present invention.

The composition may contain an effective amount of an inhibitor of mTOR as an active ingredient. The inhibitor of mTOR may be any material having the activity to prevent PLD from binding to raptor, thereby inhibiting the formation of a complex of PLD and mTOR through raptor. The inhibitor of mTOR may be any material capable of inactivating the raptor binding domain of PLD by various means as aforementioned. Alternatively, the inhibitor of mTOR may be a compound screened by the screening method according to the present invention.

The mTOR-related metabolic diseases may include cancer, diabetes, obesity, hamartoma syndrome including tuberous sclerosis complex, Peutz-Jeghers syndrome, Cowden disease, tissue/organ hypertrophy including cardiac hypertrophy, etc.

In terms of sensing mitogenic signal as a form of PA through complex formation, this appears an efficient means of responding quickly and specifically. Moreover, the coordinated organization of multiple proteins by scaffold proteins is important for signaling efficiency and specificity, as exemplified in KSR-mediated MAPK regulation (Raabe, T., Rapp, U. R. Science's STKE (2002) http://www.stke.org/cgi/content/full/sigtrans;2002/136/pe28, which is incorporated herein as an reference). KSR, a kinase suppressor of Ras, functions as a scaffold and thus helps assemble MAPK pathway components into a localized signaling complex. It is likely that the interaction of the upstream regulator (i.e., PLD2) with scaffold (i.e., raptor) is also important for localized mTOR signaling complex, since downstream effectors (i.e., S6K1 and 4EBP1) use same scaffold (i.e., raptor) to localize at the mTOR complex. Furthermore, it has been reported that various proteins as well as mTOR can interact with PA. Interestingly, in the present invention, the novel role of PLD2 in the regulation of the other PA binding proteins, such as mTOR, is examined.

Figure 6:
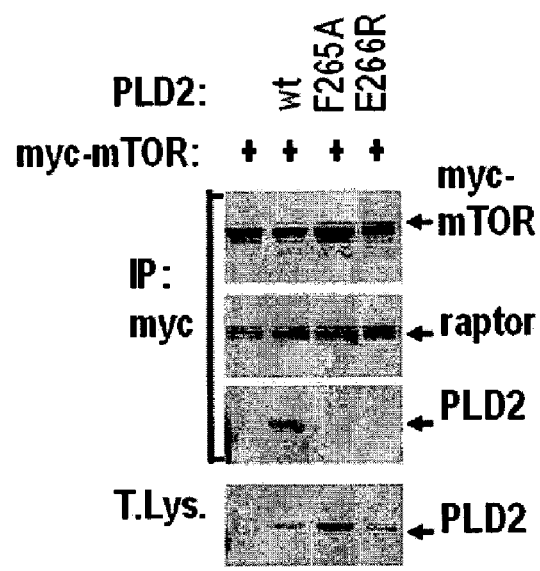
FIG. 6 shows various TOS motif patterns and the electrophoresis results for various mutants thereof.
Figure 11:
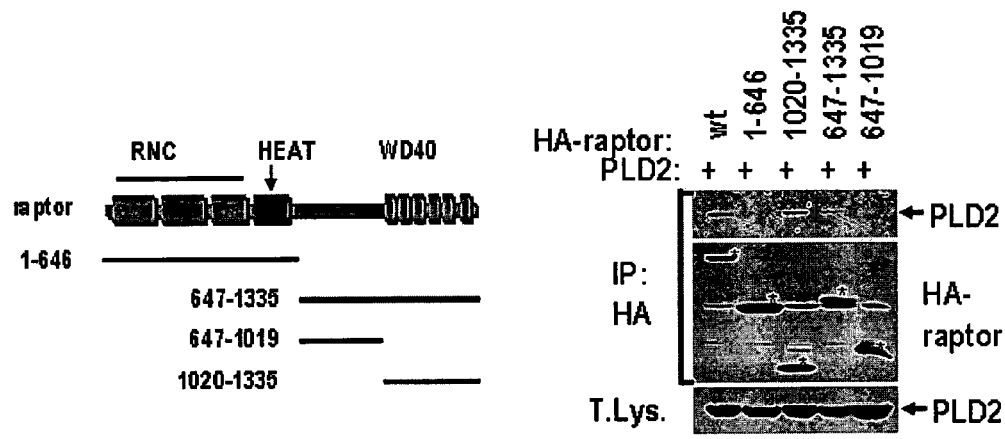
FIG. 11 shows a schematic view of raptor and its truncated fragments for site mapping analysis, and electrophoresis results of interaction between PLD2 and the various raptors.

S6K1 and 4EBP1 use their TOS motifs to interact with raptor in similar ways, and therefore compete with each other for binding to raptor (FIG. 6). However, in the present invention, PLD2 is found to share raptor with S6K1 or 4EBP1 despite their possessing a TOS motif-like sequence. The present invention find that the PLD2 binding site in raptor is the amino acids 1020-1335 of the full-length raptor (SEQ ID NO: 5) encompassing WD40 repeat at C-terminus (FIG. 11). It is not clear why PLD2 favor the C-terminal WD40 domain to bind to raptor, and it is possible that PLD2 has additional binding motifs that interact with this domain.

Although over-expression of PLD1 as well as PLD2 activates the mTOR pathway in HEK293 cells, mTOR is likely to interact with PLD2 only, which implies an alternative pathway for the PLD1-dependent activation of the mTOR pathway, possibly through Cdc42/S6K1 signaling. This results also show that the silencing effect of PLD1 on mTOR signaling is modest and completely rescued by PA treatment, whereas PLD2 effect on mTOR signaling is not rescued by exogenous PA treatment, demonstrating an obvious difference between PLD1 and PLD2. Moreover, it is possible that PLD2 is under the control of PLD1 since PLD1 signals PLD2 through phosphoinositide 4-phosphate 5 kinase.

Knowledge about the molecular mechanism by which the mTOR pathway is regulated by cellular nutritional states and how impairment of the pathway leads to metabolic diseases, such as cancer, obesity, diabetes, hamartoma syndrome including tuberous sclerosis complex, Peutz-Jeghers syndrome, Cowden disease, tissue/organ hypertrophy including cardiac hypertrophy, etc., is critically required. The findings of the present invention may be the first step toward attainment of such knowledge. This may be supported by the determination of Rheb-mediated regulation of the mTOR pathway. Interaction of PLD2 with Rheb is stabilized in nutrient-rich condition. Also, interaction of PLD2 with raptor is stabilized in nutrient-rich condition. It may be speculated that these two interactions are a regulatory point for nutrient-induced mTOR activation. Identification of molecular mechanism may provide an important understanding how nutrient impinges on the mTOR complex.

Enhancement of PA production has been reported in various cancer tissues and tumors including prostate cancer and breast cancer. In most cases, this is correlated with overexpression of PLD. However, the mechanism how this is related with tumorigenesis has not been suggested. Our identification of the role of PLD2 in the mTOR signaling suggests the potential molecular mechanism for PLD2-mediated tumorigenesis.

The present invention is further explained in more detail with reference to the following examples. These examples, however, should not be interpreted as limiting the scope of the present invention in any manner.

EXAMPLE

Example 1

Preparation of Materials

The materials used in the following examples were as follows:

The enhanced chemiluminescence kit and dipalmitoylphosphatidyl [methyl-$^3$H]choline were purchased from Amersham Biosciences. Horseradish peroxidase-conjugated goat anti-rabbit IgG and goat anti-mouse IgA, IgM, and IgG were from Kirkegaard & Perry Laboratories, Inc. (Gaithersburg, Md.). Polyclonal antibody was raised against PLD as previously described in "Lee, T. G., Park, J. B., Lee, S. D., Hong, S., Kim, J. H., Kim, Y., Yi, K. S., Bae, S., Hannun, Y. A., Obeid, L. M. et al. Biochim. Biophys. Acta 1347 (1997) 199", which is hereby incorporated by reference. Antibodies against mTOR, pS6K1 (pThr 389), S6K1, p4EBP1(pThr 37/46), and 4EBP1 and rapamycin were from Cell Signaling Technology (Beverly, Mass. Polyclonal raptor antibody was a generously gift from Dr. David M. Sabatini (MIT, USA). Protein A-Sepharose was from RepliGen (Needham, Mass.). CHAPS was from Sigma. Dulbecco's modified Eagle's medium (DMEM) and LipofectAMINE were from Invitrogen. C-6 phosphatidic acid was from Avanti, and recombinant 4EBP1 was purchased from Stratagen. Cells and vectors used the following examples were obtained from Invitrogen, unless differently mentioned.

Example 2

Preparation of Plasmids

Mammalian expression vectors for PLD1$^{wt}$, PLD2$^{wt}$, PLD2$^{\Delta N184}$, PLD2$^{\Delta N308}$, and PLD2$^{K758R}$ were used as described in "Park, J. B., Kim, J. H., Kim, Y., Ha, S. H., Yoo, J. S., Du, G., Frohman, M. A., Suh, P. G., Ryu, S. H. J. Biol. Chem. 275 (2000) 21295," "Kim, J. H., Kim, J. H., Ohba, M., Suh, P. G., Ryu, S. H. Mol. Cell. Biol. (2005) 3194" and "Lee, J. S., Kim, J. H., Jang, I. H., Kim, H. S., Han, J. M., Kazlauskas, A., Yagaisawa, H., Suh, P. G., Ryu, S. H. J. Cell Sci. 118 (2005) 4405," which are incorporated herein as referenced. Expression vectors for HA-mTOR$^{wt}$, myc-mTOR$^{wt}$, myc-raptor$^{wt}$, HA-raptor$^{wt}$ and HA-raptor$^{194YDC/AAAmt}$ were gifts from Dr. David M. Sabatini (MIT) (Kim, D. H., et al. mTOR interacts with raptor to form a nutrient-sensitive complex that signals to the cell growth machinery. *Cell* 110, 163-175 (2002), which is hereby incorporated by reference). To introduce the TOS-motif mutation in PLD2, pCDNA3.1(+)/PLD2 containing wild type PLD2 was PCR amplified using the following oligomers; sense (5'GGC CGA GAC CAA GTT TGT TAT CGC3'; SEQ ID NO: 6), antisense (F265A: 5'CCA TCG ATC CGC ACG CCG TGC CGT GCC TCC GTG CTC CTT TTC CCC ACT TGC ACC TCA GCG CCA GG3'; SEQ ID NO: 7), antisense (E266R: 5'CCA TCG ATC CGC ACG CCG TGC CGT GCC TCC GTG CTC CTT TTC CCC ACT TGC ACC CTA AAG CCA GG3'; SEQ ID NO: 8). DNA fragments generated by PCR and pCDNA3.1(+)/PLD2(WT) were treated with XhoI and Cla I.

Example 3

RNA Interference

Pairs of 21-nucleotide sense and antisense RNA oligomers were synthesized and annealed by Dharmacon Research, Inc.

(Lafayette, Colo.). The oligonucleotides used for PLD2 were: sense, 5'-AAG AGG UGG CUG GUG GUG AAG-3' (SEQ ID NO: 9) and antisense, 5'-CUU CAC CAC CAG CCA CCU CUU-3' (SEQ ID NO: 10), which correspond to human PLD2 coding nucleotides 703-723. The oligonucleotides used for PLD1 were: sense, 5'-AAG GUG GGA CGA CAA UGA GCA-3' (SEQ ID NO: 11), and antisense, 5'-UGC UCA UUG UCG UCC CAC CUU-3' (SEQ ID NO: 12), which correspond to human PLD1a coding nucleotides 1455-1475. All siRNA sequences were subjected to BLAST in the NCBI database and complete matches were only found for PLD2 sequences. Luciferase GL2 duplex was purchased from Dharmacon Research, Inc. and was used as a negative control. For add-back experiment for PLD2 silencing, three residues of human PLD2 cDNA (nucleotides 703-723 of PLD2; AAGAG GTGGCTGGTGGTGAAG; SEQ ID NO: 13) are substituted to AAGAḠAT̄Ḡ̄GCTAGTAGTGAAG for addback mutants of PLD2$^{wt}$ (Kim, J. H., Kim, J. H., Ohba, M., Suh, P. G., Ryu, S. H. Mol. Cell. Biol. 25 (2005) 3194, which is hereby incorporated by reference). This mutation is silencing mutations. This gene is subcloned into mammalian expression vector pcDNA3.1 (Invitrogen) and digested with restriction enzymes KpnI and XbaI. These mutations are confirmed through nucleotide sequence analysis.

Example 4

Cell Culture and Plasmid/siRNA Transfection

COS7 cells (ATCC, CRL-1651) were maintained in a 5% CO2 humidified atmosphere at 37° C. and fed DMEM supplemented with 10% bovine calf serum (HyClone). HEK293 cells (ATCC, CRL-1573) and OVCAR-3 cells (ATCC, HTB-161) were fed DMEM supplemented with 10% fetal bovine serum (HyClone). Cells grown on tissue culture dishes was transiently transfected using LipofectAMINE, as described in "Kim, J. H., Kim, J. H., Ohba, M., Suh, P. G., Ryu, S. H. Mol. Cell. Biol. 25 (2005) 3194" and "Lee, J. S., Kim, J. H., Jang, I. H., Kim, H. S., Han, J. M., Kazlauskas, A., Yagaisawa, H., Suh, P. G., Ryu, S. H. J. Cell Sci. 118 (2005) 4405," which are hereby incorporated by reference. Cells were allowed to express the recombinant proteins for 24 hr after transfection and then deprived of serum for additional 24 hr. The cells were then subjected to co-immunoprecipitation analysis. For knockdown with siRNA, cells were grown for 36-48 hrs before serum deprivation.

Example 5

Co-Immunoprecipitation

After harvesting COS7 cells, total extracts were prepared by brief sonication in ice-cold lysis buffer (40 mM HEPES pH7.5, 120 mM NaCl, 1 mM EDTA, 10 mM pyrophosphate, 10 mM glycerophosphate, 50 mM NaF, 1.5 mM Na$_3$VO$_4$, 0.5% CHAPS, 1 mM PMSF, protease inhibitor cocktails). Clarified extracts were mixed with 2 µg of the respective antibodies. Then protein A-Sepharose beads were added to isolate the antibody complex. After four washings with lysis buffer, the final immunoprecipitates were washed once with wash buffer (50 mM HEPES pH7.5, 150 mM NaCl), and then subjected to SDS-PAGE using Hyperfilm (Amersham Pharmacia Biotech), nitrocellulose membranes (Watmann), Power supply (Amersham Pharmacia Biotech), Electrophoretic Transfer unit (Hoefer Scientific Instruments), and ECL™ (Amersham Pharmacia Biotech).

Example 6

Western Blot Analysis

Proteins were separated by SDS-PAGE on 8-16% gradient gels, and the separated proteins were transferred onto nitrocellulose membranes and blocked with TTBS buffer (10 mM Tris-HCl, pH 7.6, 150 mM NaCl, and 0.05% Tween-20) containing 5% skimmed milk powder. The SDS-PAGE was performed using Hyperfilm (Amersham Pharmacia Biotech), nitrocellulose membranes (Watmann), Power supply (Amersham Pharmacia Biotech), Electrophoretic Transfer unit (Hoefer Scientific Instruments), and ECL™ (Amersham Pharmacia Biotech). Membranes were then incubated with primary antibody at the concentration recommended by the manufacturer for 4 hr at room temperature. Unbound antibody was washed away with TTBS buffer. Membranes were subsequently incubated with horseradish peroxidase-conjugated secondary antibody for 1 hr at room temperature, washed five times with TTBS buffer, and developed using an ECL system.

Example 7

In Vivo PLD Assay

In vivo PLD activity was assayed by measuring the formation of phosphatidyl-butanol as described in "Lee, J. S., Kim, J. H., Jang, I. H., Kim, H. S., Han, J. M., Kazlauskas, A., Yagaisawa, H., Suh, P. G., Ryu, S. H. J. Cell Sci. 118 (2005) 4405," which is hereby incorporated by reference. In brief, cells were loaded with [$^3$H]myristic acid (2 µCi/ml) for 8 hrs and then washed twice with DMEM. Labeled cells were incubated with 0.4% butanol for 10 min to measure basal PLD activity. Total lipids were extracted with 1.2 ml of methanol:1 M NaCl:chloroform (1:1:1 by volume) and then separated by thin-layer chromatography on silica gel plates. The amount of [$^3$H]phosphatidyl-butanol formed was expressed as a percentage of total [$^3$H]lipid to account for cell labeling efficiency differences.

Example 8

In Vitro Kinase Assay for mTOR Activity

Recombinant myc-mTOR was expressed with the indicated proteins and then immunoprecipitated using anti-myc antibody, as previously described in Kim, D. H., Sarbassov, D. D., Ali, S. M., King, J. E., Latek, R. R., Erdjument-Bromage, H., Tempst, P., Sabatini, D. M. Cell 110 (2002) 163, which is hereby incorporated by reference. Recombinant 4EBP1 (Stratagen) was used as a substrate for in vitro kinase assays. Activities were measured using anti-phospho-4EBP1 antibody (phosphor-37/46). The kinase assay was performed by mixing buffer containing 25 mM Hepes pH7.4, 50 mM KCl, 10 mM MgCl$_2$, 4 mM MnCl$_2$, 20% glycerol, 2 mM DTT, 0.1 mM ATP, 1 µg 4EBP1 with the indicated immunoprecipitates and then incubated at 30° C. for 15 min.

Example 9

Examination of mTOR Activation by PLD2

Figure 1:
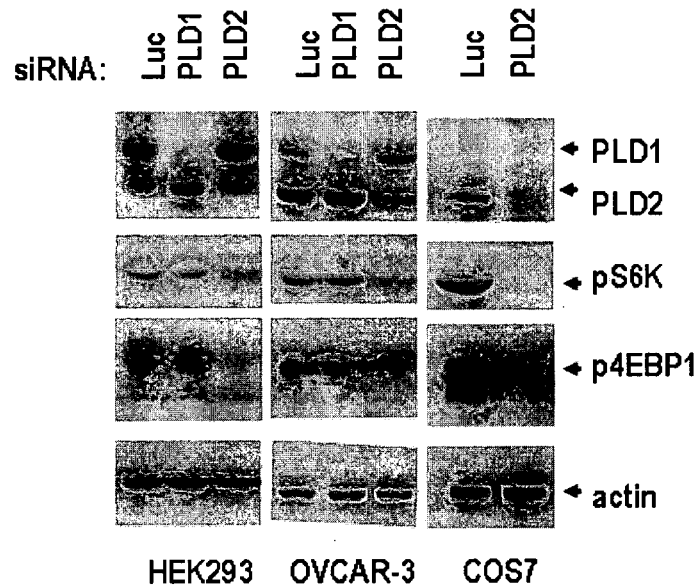
FIG. 1 shows electrophoresis results of phosphorylation of S6K1 and 4EBP1 in various PLD 1 or PLD2 knockdown cells.

PLD hydrolyzes phosphatidylcholine to generate PA and this process constitutes a link whereby mitogenic signals impinge on the mTOR pathway. However, the mechanism by which PA activates mTOR in cells remains unknown. To gain further insight into this process, the present example compared the effects of two mammalian PLD isozymes, PLD1 and PLD2, on mTOR activation using isozyme-specific siRNAs in human embryonic kidney (HEK) 293 cells, human ovarian cancer-derived OVCAR-3 cells, and monkey epithelial COS7 cells.

siRNAs for PLD1 or PLD1 were transfected into HEK293, OVCAR-3, and COS7 cells, respectively, using lipofectamine, as described in Examples 3 and 4. After 36 hrs, cells were deprived of serum for 24 hrs, and then were lysed in CHPAS-containing lysis buffer (Sigma), as described above. siRNA for luciferase was used as a negative control. Equal protein loadings were verified versus actin. Then, the phosphorylations of S6K1 and 4EBP1 in the cells were examined and the obtained results are shown in FIG. 1. As shown in FIG. 1, the knockdown of PLD2 dramatically reduced the phosphorylations of S6K1 and 4EBP1, well-known mTOR effectors, as compared with those of PLD1 knockdown. The results suggest that PLD has an essential role in mTOR activation.

Figure 2:
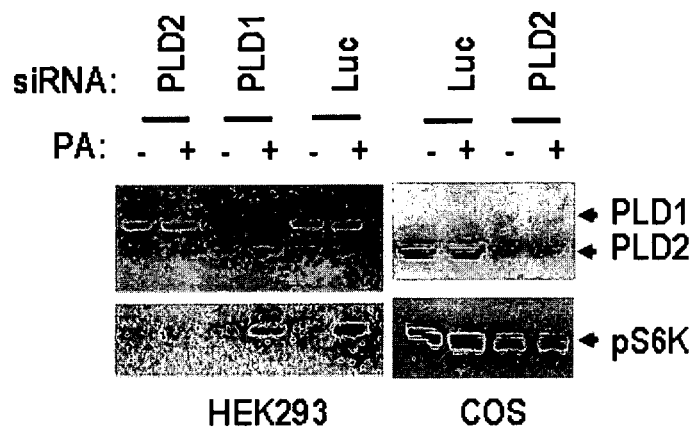
FIG. 2 shows electrophoresis results of phosphorylation of S6K1 in various PLD 1 or PLD2 knockdown cells when PA is exogenously added.

Next, another experiment was conducted to test whether exogenous PA can rescue mTOR signal abrogation in PLD2-knocked-down cells. HEK293 and COS7 cells were transfected with the indicated siRNAs using lipofectamine. After 36 hrs, cells were deprived of serum for 24 hrs. 100 µM of C-6 PA solubilized in DW was then treated for 30 min. Resulting lysates were subject to SDS-PAGE. The SDS-PAGE results were shown in FIG. 2.

The inventor reasoned that if the role of PLD2 in mTOR activation is solely that of PA generation, then the exogenous addition of PA should completely rescue mTOR signaling despite PLD2 expression. However, according to FIG. 2, to is found that PA could not trigger S6K1 phosphorylation in PLD2-knocked-down HEK293 and COS7 cells. Summarizing, the isozyme-specific knockdown of PLD by using siRNA suggests that PLD2 has a profound role in mTOR signaling, and that PLD2 might have another mechanism to activate mTOR signaling in accord with PA generation.

Example 10

Formation of a Complex of PLD2 with mTOR through PLD2's TOS Motif-Like Sequence

This example investigated the reason why PA could no longer activate mTOR in the absence of PLD2 expression. One possibility concerns the proximity of PLD2 around the mTOR complex. PA contains a long acyl chain that might restrict its membrane mobility; moreover, PA is a transient species. These properties of PA encouraged the inventors to speculate that mTOR might be localized near PLD to monitor the PA produced in response to upstream signals; moreover, such a possibility suggests the existence of a physical connection between mTOR complex and PLD.

Figure 3:
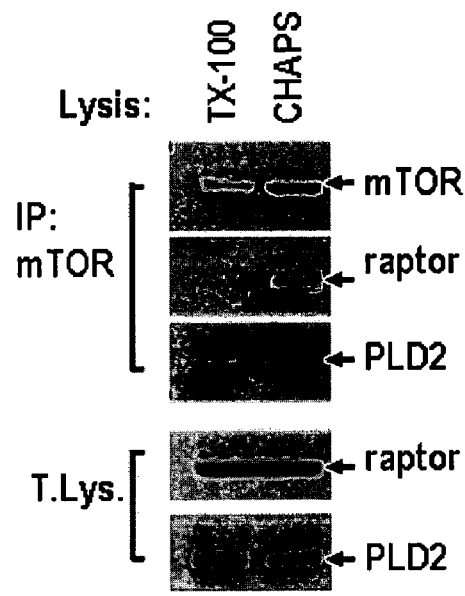
FIG. 3 shows electrophoresis results of interaction between PLD2, mTOR and raptor in COS7 cells.

To test this possibility, endogenous mTOR was immunoprecipitated with anti-mTOR antibody. COS7 cell lysates (10 mg) were prepared under different lysis conditions using Triton X-100 or CHPAS and then subjected to co-IP (immunoprecipitation) analysis against anti-mTOR antibody, as described above Examples 1 to 5. Resulting immunoprecipitates were subjected to SDS-PAGE. The obtained results were shown in FIG. 3 (arrows indicate the positions of blotted protein). As shown in FIG. 3, it was found that these immunoprecipitates from COS7 and HEK293 contained endogenous PLD2. The interaction between mTOR and PLD2 was sensitive to Triton X-100, but stable in CHAPS-containing lysis conditions, similarly to the mTOR-raptor interaction.

Figure 4:
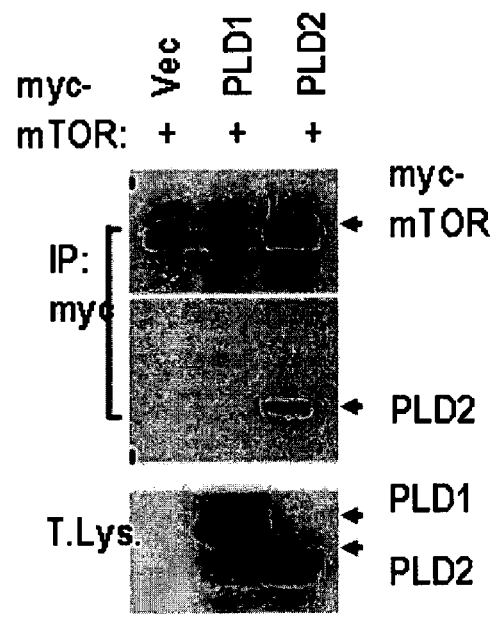
FIG. 4 shows electrophoresis results of interaction between recombinant mTOR and PLD1 or PLD2.

Further, lysates from COS7 cells overexpressing myc-mTOR above and PLD1 or PLD2 were co-immunoprecipitated with anti-myc antibody and immunoblotted with anti-PLD antibody, as described above Examples 1 to 5. The obtained SDS-PAGE results were shown in FIG. 4. As shown in FIG. 4, recombinant PLD2 also formed a complex with recombinant mTOR, and this interaction was specific for PLD2 as recombinant PLD1 did not interact with mTOR. The recombinant PLD2 was prepared by expressing hPLD2 in a baculovirus expression system and purifying the expressed product from detergent extracts of baculovirus-infected Sf9 cells (Invitrogen) using chelating Sepharose affinity column chromatography. The recombinant myc-mTOR was expressed and immunoprecipitated using anti-myc antibody.

Figure 5:
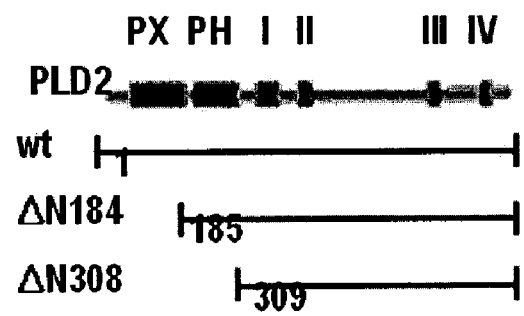
FIG. 5 shows schematic views of PLD2 and its N-terminal truncated fragment for site mapping analysis.
Figure 5:
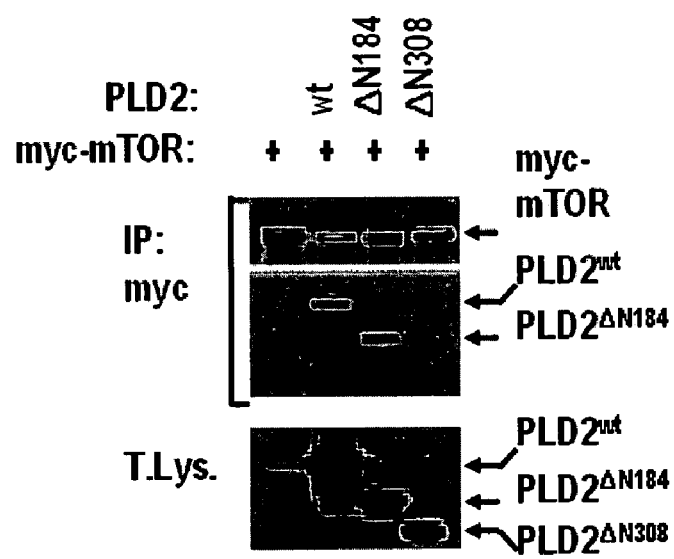

To identify the region of PLD2 responsible for the interaction with mTOR, N-terminal truncated PLD2 fragments were prepared as described in "Park, J. B., Kim, J. H., Kim, Y., Ha, S. H., Yoo, J. S., Du, G., Frohman, M. A., Suh, P. G., Ryu, S. H. J. Biol. Chem. 275 (2000) 21295," which is hereby incorporated by reference, and used for site-mapping analysis. The process resulted in the identification of a PH domain-containing region in PLD2 (i.e., a.a. 185-308). The obtained schematic view of PLD2 was shown in upper panel of FIG. 5, showing a schematic view of PLD2 N-terminal deleted fragments versus whole PLD2. Then, myc-mTOR$^{wt}$ was transfected with the indicated PLD2 fragments and co-IP analysis was performed as above. The obtained results were shown in lower panel of FIG. 5 (IP; immunoprecipitation, T. Lys.; Total lysates), showing that the immunoprecipitation of mTOR is generated when using wild-type PLD2 or ΔN184 PLD2 (184 amino acid residues at N-terminus are deleted), but not when using ΔN308 PLD2, indicating that the raptor bonding site of PLD2 resides between 185 and 308 amino acid residues.

Interestingly, in PLD2, but not in PLD1, this region was found to contain FEVQV (a.a. 265-269 of PLD2; SEQ ID NO: 4), which is a TOS motif pattern present in both S6K1 and 4EBP1 that allows binding with mTOR through raptor (FIG. 6 upper panel; TOS motifs of human 4EBP1 and human S6K1 were compared with the putative TOS motif in human/rat/mouse PLD2. Corresponding regions in human/rat/mouse PLD1 are shown and asterisks are used to highlight differences). Therefore, point mutants, PLD2$^{F265A}$ and PLD2$^{E266R}$ were prepared and examined their binding with mTOR. myc-mTOR was expressed with the indicated PLD2 mutants and the resulting lysates were subjected to co-IP analysis. Endogenous raptor was immunoblotted with anti-raptor polyclonal antibody described above. The obtained results were shown in lower panel of FIG. 6. It was found that both of these PLD2 point mutants abrogated its interaction with mTOR, thus supporting the notion that these residues are important for PLD2-mTOR binding, and that they constitute a TOS motif, as found in S6K1 and 4EBP1.

Example 11

Formation of a Complex of PLD2 with mTOR through Raptor mTOR exists as two protein complexes in mammalian cells, i.e., cell growth-related mTOR functions in cooperation with raptor, whereas cytoskeletal organization-related mTOR function cooperates with rictor/mAVO3. The finding of Example 10 regarding a TOS motif-like sequence in PLD2 suggests that PLD2 may form a complex with mTOR by interacting with raptor. This example tested whether PLD2 forms a complex with mTOR by binding to raptor.

Figure 7:
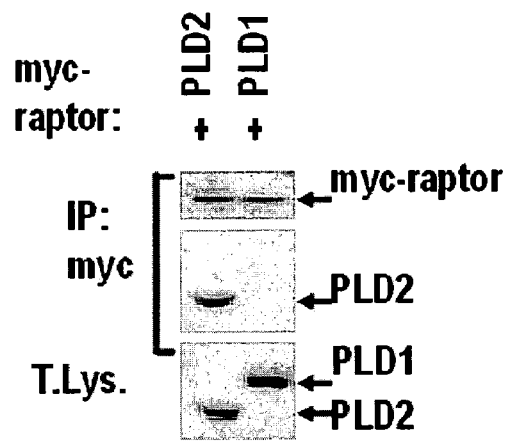
FIG. 7 shows electrophoresis results of interaction between raptor and PLD1 or PLD2.
Figure 8:
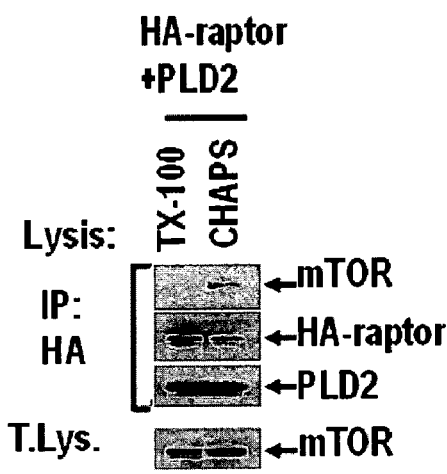
FIG. 8 shows electrophoresis results of interaction between PLD2 and raptor under Triton X-100 or CHAPS lysis condition.
Figure 9:
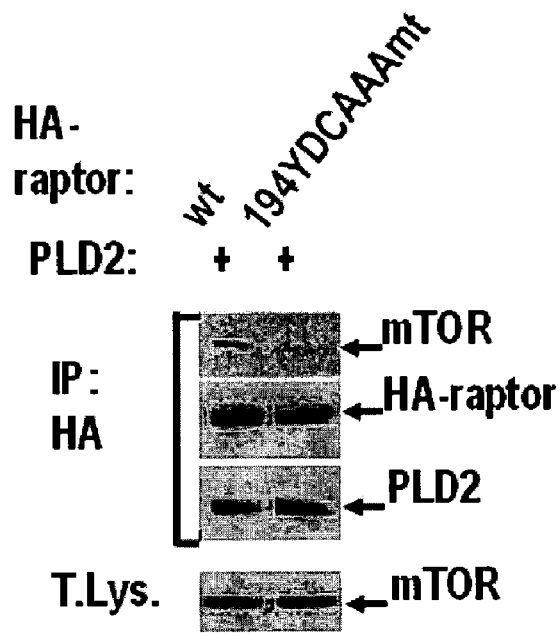
FIG. 9 shows electrophoresis results of interaction between mTOR, PLD2 and raptor.

Myc-raptor was expressed with PLD1 or PLD2 into COS7 cells as described above. Resulting lysates were prepared using Triton X-100-containing lysis conditions and then subjected to co-IP analysis. The obtained results were shown in FIG. 7. HA-raptor and PLD2 were expressed and lysed in lysis buffer containing different detergents, Triton X-100 and CHAPS, and then subjected to co-IP analysis. Endogenous mTOR was blotted by anti-mTOR antibody. The results were shown in FIG. 8. PLD2 was expressed with either HA-raptor$^{wt}$ or HA-raptor$^{194YDC/AAAmt}$ and the resulting lysates were immunoprecipitated with anti-HA antibody. Bound mTOR and PLD2 were detected by immunoblotting. The results were shown in FIG. 9. HA-raptor was expressed with the indicated PLD2 constructs into COS7 cells. Cells were lysed in lysis buffer containing Triton X-100 and then subjected to co-IP analysis using anti-HA antibody. The results were shown in FIG. 10.

Figure 10:
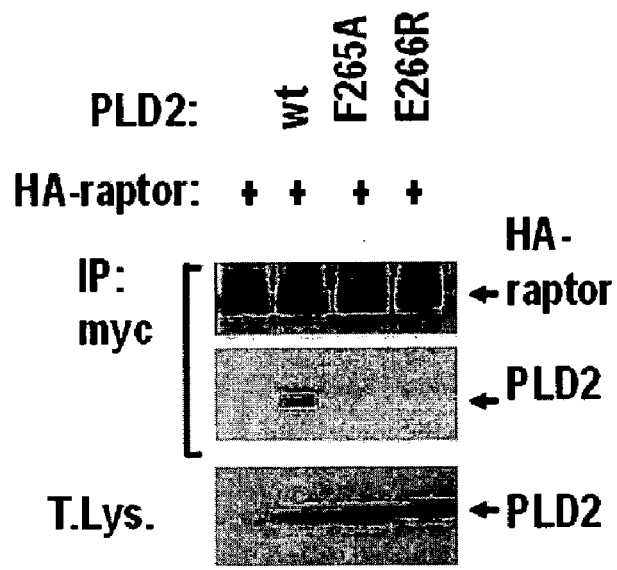
FIG. 10 shows electrophoresis results of interaction between PLD2 and raptor according to various TOR-like sequence of PLD2.

In the present example, it was found; 1) that recombinant PLD2 specifically interacts with recombinant raptor even under Triton X-100 lysis conditions (FIG. 7); 2) that the interaction between PLD2 and raptor is insensitive to Triton X-100 (FIG. 8) and that it does not require an interaction between raptor and mTOR (FIG. 9); 3) that the interaction between PLD2 and raptor under Triton X-100 lysis conditions is also dependent on TOS motif-like sequence of PLD2 (FIG. 10).

These findings raise the possibility the PLD2-raptor interaction is independent of mTOR. However, endogenous mTOR complex was found to contain raptor and PLD2 (FIG. 3), and the interaction between mTOR and PLD2 was also found to be dependent on its TOS motif-like sequence (FIG. 6). These findings strongly suggest that PLD2 forms a complex with mTOR-raptor, and that in this context raptor provides docking site for PLD2 by interacting with a TOS motif-like sequence in PLD2.

Example 12

PLD2 Binding Site in Raptor

Raptor contains a conserved N-terminal (RNC) domain, which is followed by three HEAT repeats in its central region and 7 WD40 repeats in the C-terminal portion. Moreover, these HEAT and WD40 repeats are protein-protein interaction motifs and are present in many eukaryotic proteins.

To identify the PLD2 binding sites in raptor, truncated raptor mutants were used for site mapping analysis. FIG. 11 is a schematic view of raptor fragments and whole raptor (left panel). PLD2$^{wt}$ was transfected with the indicated HA-raptor constructs and co-IP analysis was performed using anti-HA antibody, as described above. The results were shown in right panel of FIG. 11 (asterisks indicate expressed raptor fragments). It is believed that the WD40 repeat of raptor is responsible for PLD2 binding, because it was found that amino acids 1020-1335 of raptor, which encompasses the WD40 repeat, can interact with PLD2.

Then, the interaction preferences of PLD2, S6K1 and 4EBP1 for raptor were directly compared, because S6K1 and 4EBP1 primarily use their TOS motifs to interact with raptor. HA-raptor$^{1-646}$ and HA-raptor$^{1020-1335}$ were expressed with PLD2, myc-S6K1, or myc-4EBP1. After co-IP analysis with anti-HA antibody, resulting immunoprecipitates were subjected to SDS-PAGE analysis. Anti-myc antibody was used to determine myc-S6K1 and myc-4EBP1 levels. The obtained results were shown in FIG. 12 (asterisks indicate expressed raptor fragments).

Figure 12:
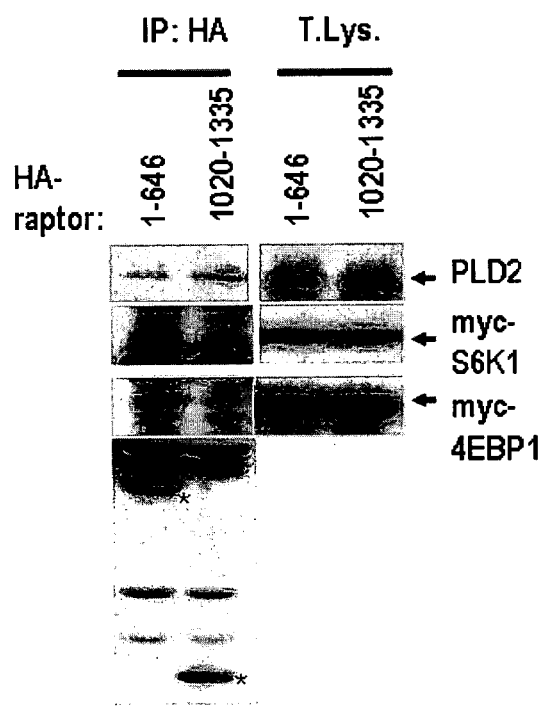
FIG. 12 shows the interaction preferences of PLD2, S6K1 and 4EBP1 for raptor.

As shown in FIG. 12, 4EBP1 were found to favor the N-terminal region (a.a. 1-646) of raptor, though they showed different preference on raptor binding with PLD2. These results raised the possibility that PLD2 forms a complex with either S6K1 or 4EBP1 through raptor.

Figure 13:
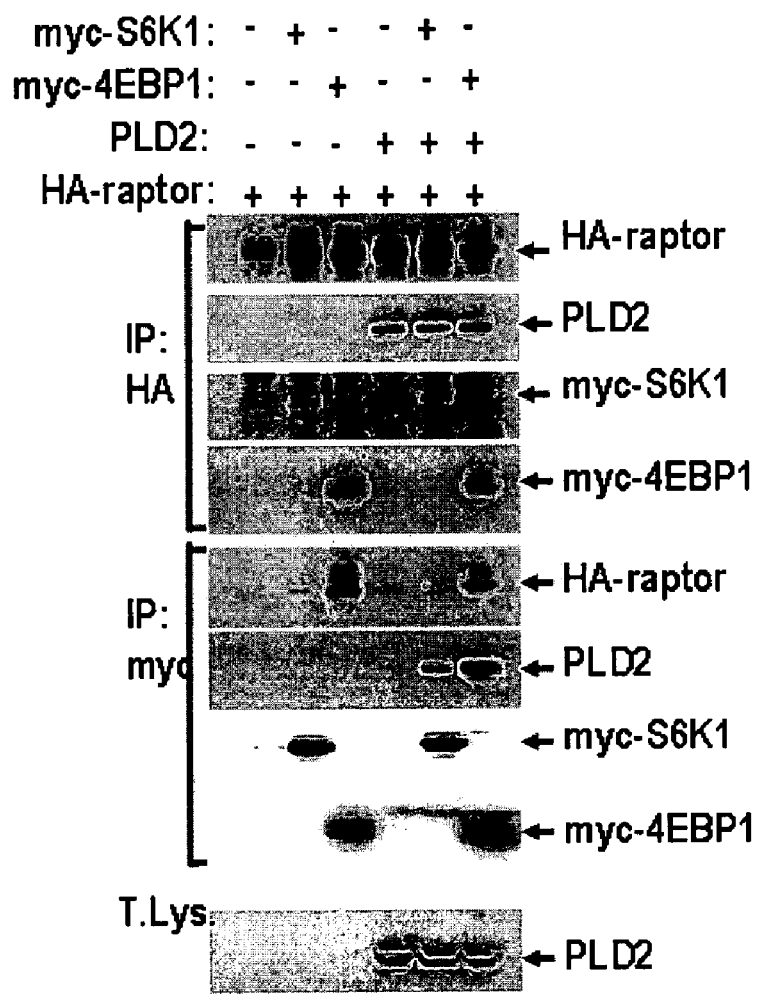
FIG. 13 shows electrophoresis results of interaction between PLD2 and S6K1 or 4EBP1 through raptor.

This was found to be the case, as PLD2 was found in raptor immunoprecipitates with S6K1 or 4EBP1 as shown in FIG. 13. The indicated recombinant proteins were expressed into COS7 cells. Resulting lysates were obtained under CHAPS-containing conditions, divided in two, and subjected to co-IP analysis with anti-HA or anti-myc antibodies. The obtained results were shown in FIG. 13. Likewise, immunoprecipitation with recombinant S6K1 or 4EBP1 also showed PLD2 bound raptor with S6K1 or 4EBP1.

Figure 14:
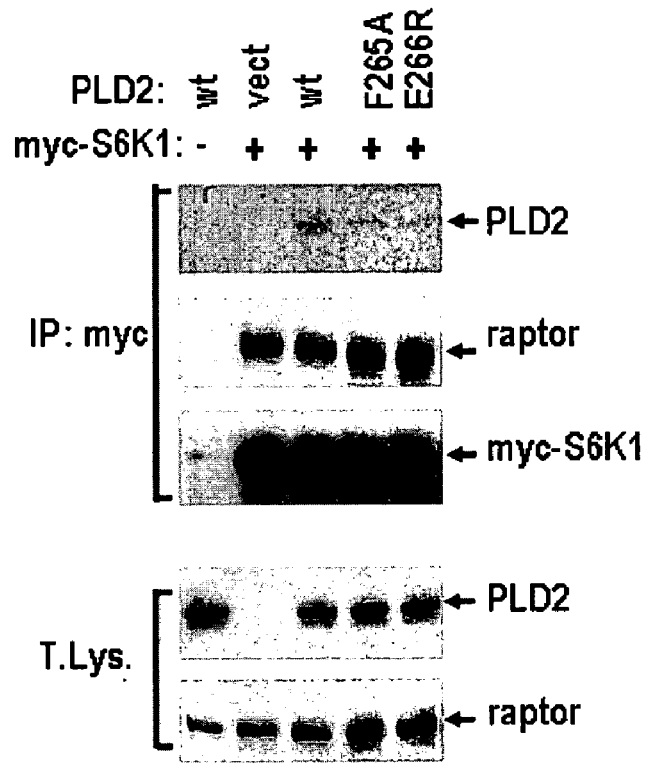
FIG. 14 shows electrophoresis results of interaction between PLD2 and S6K1 or 4EBP1 through raptor according to various TOR-like sequence of PLD2.

As expected, PLD2-raptor-S6K1 complex formation was found to require the integrity of the PLD2 TOS motif-like sequence as shown in FIG. 14. The indicated proteins were expressed in COS7 cells and the resulting lysates were subjected to co-IP analysis with anti-myc antibody. The obtained results were shown in FIG. 14. In case of S6K1 and 4EBP1, it was reported that they compete for interaction with raptor. However, PLD2 uses WD40 region of raptor to interact. Therefore, it is reasonable that PLD2 can form a complex with either S6K1 or 4EBP1 through raptor. Altogether, more detailed molecular analysis revealed that PLD2 binds the mTOR/raptor complex through raptor.

Example 13

PLD2-Raptor Interaction and Enzymatic Activity of PLD2

To determine whether the PLD2-raptor binding is an aspect of mTOR pathway activation, the ability of PLD2 point mutants to stimulate S6K1 phosphorylation was examined.

Figure 15:
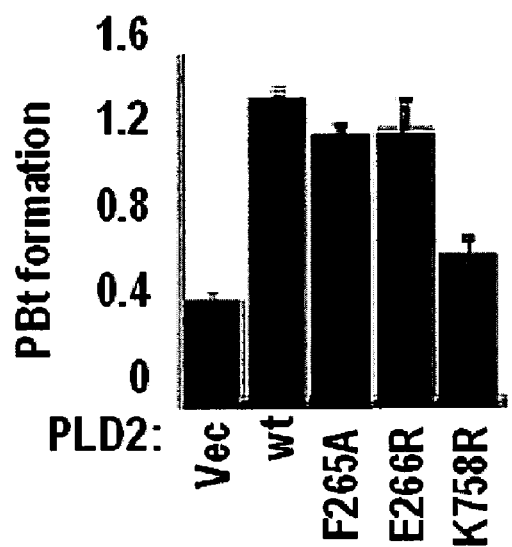
FIG. 15 shows PBt formation results according to PLD2 point mutations at TOR-like sequence.

In vivo PLD assays were performed in COS7 cells expressing the various PLD2 constructs shown in FIG. 15. The obtained PBt (phosphatidyl-butanol) formation results were shown in FIG. 15. FIG. 15 shows that PLD2$^{F265A}$ and PLD2$^{E266R}$ have similar level of enzymatic activity compared to PLD2$^{wt}$, suggesting that the localization of PLD2 at the mTOR complex is not important for its enzymatic property.

Figure 16:
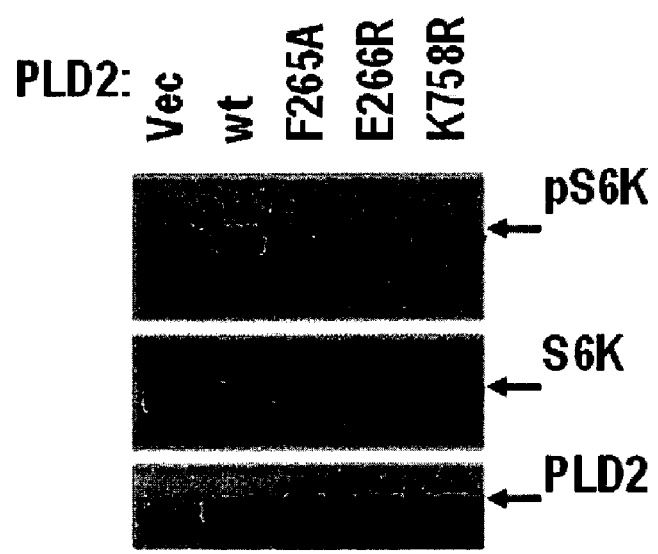
FIG. 16 shows S6K1 phosphorylation results according to PLD2 point mutations at TOR-like sequence.

However, PLD2$^{F265A}$ and PLD2$^{E266R}$ did not trigger S6K1 phosphorylation versus PLD2$^{wt}$, as shown in FIG. 16 demonstrating the results of western blot analysis of the obtained Lysates (FIG. 15).

Figure 17:
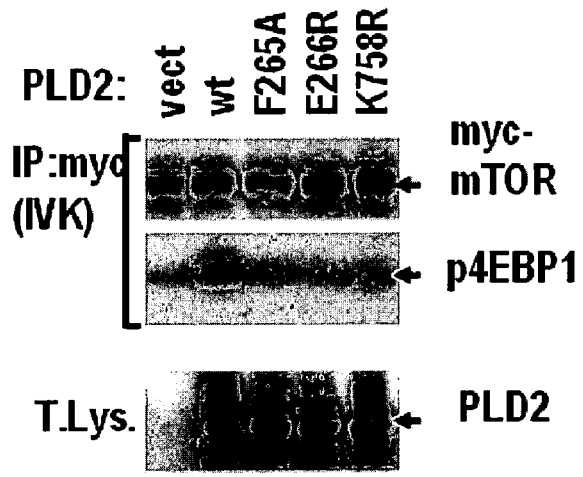
FIG. 17 shows the mTOR kinase activity according to PLD2 point mutations at TOR-like sequence.

As shown in FIG. 17, myc-tagged recombinant mTOR with the indicated PLD2 constructs was expressed. The myc-immunoprecipitate obtained was used for co-IP analysis. After co-IP analysis, myc-immunoprecipitates were subjected to in vitro kinase assays (IVK) for mTOR, as described above. The results were shown in FIG. 17. The results obtained correlated with those of S6K1 phosphorylation in as much as PLD2$^{F265A}$ and PLD2$^{E266R}$ could not trigger mTOR kinase activity. It is possible that PLD2 itself has some effect on mTOR kinase activity as was raptor or GβL. However, lipase-inactive PLD2$^{K758R}$, which is capable of binding mTOR-raptor, did not activate mTOR kinase activity, thus excluding any direct effect of PLD2 on mTOR kinase activity. In addition, this activation is not due to PA production during kinase assays, because our in vitro kinase assay did not contain phosphatidylcholine, an essential substrate for PLD. Thus this finding excludes mTOR activation by PA during these conditions. It was speculated that PLD2 activates mTOR before cell lysis via an unidentified mechanism, such as, a conformational change or a posttranslational modification.

Figure 18:
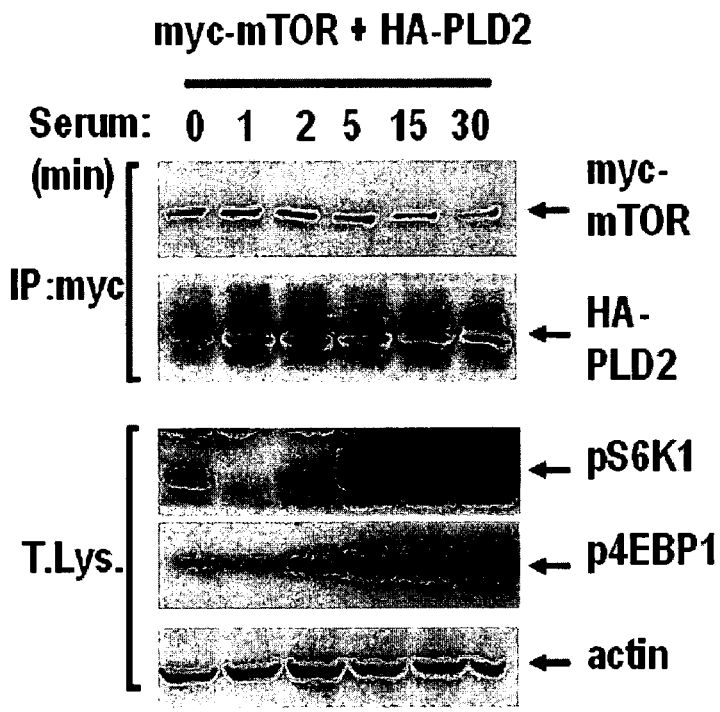
FIG. 18 shows electrophoresis results obtained from the mTOR-raptor interaction.

Myc-mTOR and HA-PLD2 were expressed in COS7 cells. After 24 hrs, cells were deprived of serum for 24 hrs and then were treated with 20% of BCS for the indicated times to stimulate mTOR signaling. After co-IP analysis with anti-myc antibody, bound HA-PLD2 was proven using anti-HA antibody. The obtained results were shown in FIG. 18. As shown in FIG. 18, the regulation of the mTOR-raptor interaction by PLD2 can be excluded because PLD2 did not have any effect on the mTOR-raptor interaction. Also, neither reducing PA generation with 1-butanol nor adding PA modulates the mTOR-raptor interaction. These results suggest that both the physical interaction between PLD2 and raptor and the enzymatic activity of PLD2 are concurrently required for mTOR pathway stimulation.

It has been reported that the mTOR-raptor interaction is not changed by mitogen stimulation (Kim, D. H., Sarbassov, D. D., Ali, S. M., King, J. E., Latek, R. R., Erdjument-Bromage, H., Tempst, P., Sabatini, D. M. Cell 110 (2002) 163, incorporated herein as a reference), which suggests the existence of unidentified mechanism to sense mitogenic signal. Various mitogens are known to activate PLD, and lead to PA production (Exton, J. H. Rev Physiol Biochem Pharmacol. 144 (2002) 1; and Cockcroft, S. Cell Mol. Life Sci. 58 (2001) 1674, which are incorporated herein as a reference).

The finding of the participation of PLD2 in mTOR activation encouraged the present inventors to determine whether PLD2 mediates the mitogenic activation of mTOR signaling.

First, the dynamicity of the PLD2-mTOR interaction was tested. As shown in FIG. 18, 20% bovine calf serum (BCS) potently increased the interaction between PLD2 and mTOR within 1 min of treatment and maintained this for 30 min. The phosphorylations of S6K1 and 4EBP1 followed at 5 min.

Figure 19:
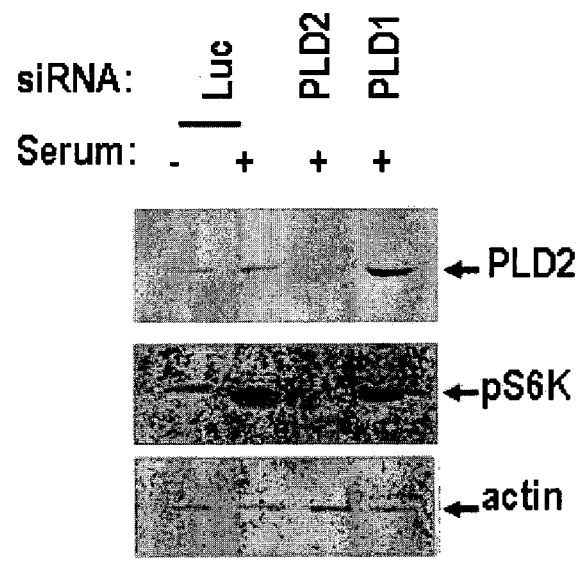
FIG. 19 shows the mitogen-dependent phosphorylation of S6K1 in PLD knockdown cells.

The indicated siRNAs were transfected into COS7 cells, and 36 hrs later, cells were deprived of serum for 24 hrs. 20% of BCS was then treated and the resulting lysates were subjected to SDS-PAGE. The results were shown in FIG. 19. As expected, knockdown of PLD2 profoundly reduced the mitogen-dependent phosphorylation of S6K1, whereas PLD1 knockdown had only a modest effect on S6K1 phosphorylation, thus supporting the notion that PLD2 is a mainly involved in mitogen-induced mTOR signaling.

Figure 20:
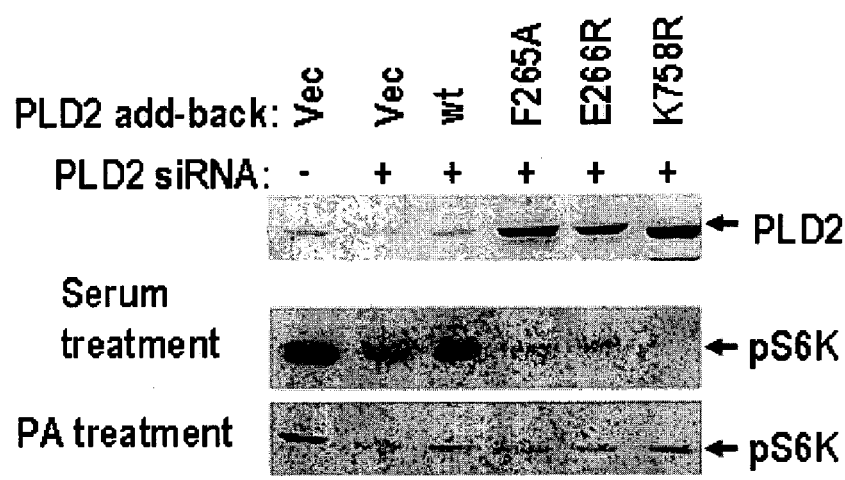
FIG. 20 shows the mitogen-dependent phosphorylation of S6K1 according to PLD2 point mutations at TOR-like sequence.

To further check the importance of PLD2 in mitogen-dependent mTOR signaling, PLD2 expression was rescued using siRNA-resistant expression constructs. PLD2 siRNAs were transfected with the indicated PLD2 add-back constructs as described in Experimental Procedures. 20% of BCS or 100 μM of C-6 PA was used to stimulate mTOR signaling. The obtained results were shown in FIG. 20. As shown in FIG. 20, it was found that mitogen-induced S6K1 phosphorylation was rescued only by $PLD2^{wt}$. Adding-back of $PLD2^{F265A}$, $PLD2^{E266R}$, and $PLD2^{K758R}$ did not rescue S6K1 phosphorylation attenuation in PLD2-knocked-down cells. Interestingly, the exogenous PA-dependent phosphorylation of S6K1 was rescued by $PLD2^{wt}$ and $PLD2^{K758R}$, but not by $PLD2^{F265A}$ and $PLD2^{E266R}$, which again highlighted the requirement for PLD2 interaction with raptor, and PA production at the mTOR complex for PLD2-dependent mTOR activation.

Example 14

Investigation of Nutrient Dependent PLD2 Activation

The above examples suggest that both the PLD2/raptor interaction and the enzymatic activity of PLD2 are required for mTOR pathway stimulation. Again, these relations suggest that PLD2 is a new binding protein that has physical and functional connections with the mTOR complex.

Until now, the function of PLD2 in nutrient signaling has not been proposed. To this end, the importance of PLD2 in nutrient signaling was tested. The stimulatory effect of leucine on S6K1 was significantly reduced by 1-butanol. Based on the result, PLD2 activity in response to nutrient levels was checked. $PLD2^{wt}$ was transfected and allowed to express for 24 hr. After serum-deprivation for 16 hr and labeling with [$^3$H]myristic acid (2(Ci/ml) for 8 hr, cells were treated with rapamycin (20 nM), D-PBS, and leucine-free media. After 45 min, same treatments including leucine-added media were added with 0.4% 1-butanol to measure PBt formation. The obtained results were shown in FIG. 21, indicating that PLD2 activity was reversibly regulated by amino acid levels, especially by leucine levels.

Figure 22:
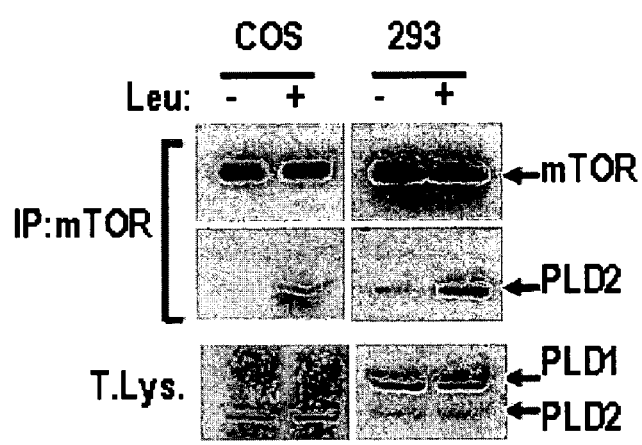
FIG. 22 shows IP analysis results using anti-mTOR antibody in COS7 and HEK293 cells in presence or absence of leucine.

To reveal the relationship between PLD2 activity and complex formation, the interaction between PLD2 and mTOR was tested. mTOR inhibition by rapamycin, which is a mTOR specific inhibitor, had no effect on the interaction between PLD2 and mTOR. However, the interaction between endogenous PLD2 and endogenous mTOR complex was increased by leucine treatment in leucine-deprived COS7 and HEK293 cells as shown FIG. 22. The results in FIG. 22 were obtained by lysing confluent COS7 and HEK293 cells and immuno-precipitating with anti-mTOR antibody after treating leucine-deprived cells with leucine.

Figure 23:
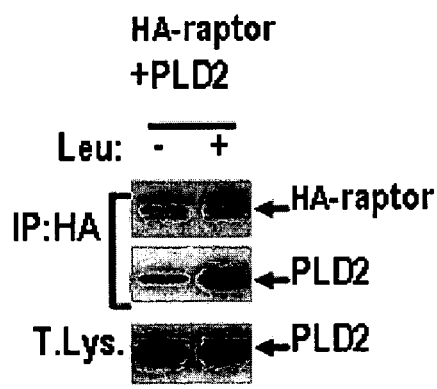
FIG. 23 shows the western blot analysis results in HA-raptor$^{wt}$/PLD2$^{wt}$ transfectant after leucine treatment.

Either HA-raptor$^{wt}$/PLD2$^{wt}$ was transfected into HEK293 cells, and the cells were subjected to leucine deprivation. Co-IP after leucine treatment was followed by Western blot analysis. The results were shown in FIG. 23. The increase by leucine was attributed to enhanced binding between PLD2 and raptor, as shown in FIG. 23. Importantly, the interaction between Rheb and PLD2 was also regulated by nutrient levels such that this interaction was stabilized under high nutrient conditions and weakened under low nutrient conditions, which allowed a nutrient-dependent mTOR complex composed of mTOR, raptor, PLD2, and Rheb to be identified. These results are well correlated with reversible regulation of PLD2 activity against the level of leucine.

What is claimed is:

1. A method of inhibiting mTOR by inhibiting the interaction between PLD2 and raptor, thereby inhibiting the formation of a complex of PLD2 and mTOR through raptor (PLD/raptor/mTOR complex), comprising the step of inactivating a raptor binding domain of PLD2 by substitution of one or more amino acids of SEQ ID NO: 4 comprised in the raptor binding domain of PLD2, with at least one other amino acid selected from the group consisting of alanine, isoleucine, leucine, methionine, phenylalanine, proline, tryptophan, valine, asparagine, cysteine, glutamine, glycine, serine, threonine, tyrosine, aspartic acid, glutamic acid, arginine, histidine, and lysine.

2. The method according to claim 1, wherein the step of inactivating a raptor binding domain of PLD2 is conducted by substitution of one or more amino acids located in the amino acid sequence of SEQ ID NO: 4 comprised in the raptor binding domain of PLD2, with alanine, or arginine.

* * * * *

SEQUENCE LISTING

<160> NUMBER OF SEQ ID NOS: 13

<210> SEQ ID NO 1
<211> LENGTH: 2549
<212> TYPE: PRT
<213> ORGANISM: Artificial Sequence
<220> FEATURE:
<223> OTHER INFORMATION: Amino acid sequence of mammalian target-of-rapamycin (mTOR) [Homo sapiens]

<400> SEQUENCE: 1

```
Met Leu Gly Thr Gly Pro Ala Ala Thr Ala Ala Thr Thr Ser
  1               5                  10                  15

Ser Asn Val Ser Val Leu Gln Gln Phe Ala Ser Gly Leu Lys Ser Arg
             20                  25                  30

Asn Glu Glu Thr Arg Ala Lys Ala Ala Lys Glu Leu Gln His Tyr Val
         35                  40                  45

Thr Met Glu Leu Arg Glu Met Ser Gln Glu Glu Ser Thr Arg Phe Tyr
     50                  55                  60

Asp Gln Leu Asn His His Ile Phe Glu Leu Val Ser Ser Asp Ala
 65                  70                  75                  80

Asn Glu Arg Lys Gly Gly Ile Leu Ala Ile Ala Ser Leu Ile Gly Val
                 85                  90                  95

Glu Gly Gly Asn Ala Thr Arg Ile Gly Arg Phe Ala Asn Tyr Leu Arg
                100                 105                 110

Asn Leu Leu Pro Ser Asn Asp Pro Val Val Met Glu Met Ala Ser Lys
            115                 120                 125

Ala Ile Gly Arg Leu Ala Met Ala Gly Asp Thr Phe Thr Ala Glu Tyr
        130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Met Glu Glu
        275                 280                 285

Ile Thr Gln Gln Gln Leu Val His Asp Lys Tyr Cys Lys Asp Leu Met
290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Pro Arg Leu Ala
385                 390                 395                 400

Ala Phe Arg Pro Ser Ala Phe Thr Asp Thr Gln Tyr Leu Gln Asp Thr
                405                 410                 415
```

```
Met Asn His Val Leu Ser Cys Val Lys Lys Glu Lys Glu Arg Thr Ala
            420                 425                 430
Ala Phe Gln Ala Leu Gly Leu Leu Ser Val Ala Val Arg Ser Glu Phe
        435                 440                 445
Lys Val Tyr Leu Pro Arg Val Leu Asp Ile Ile Arg Ala Ala Leu Pro
    450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
                485                 490                 495
Ile Gln Gln Asp Ile Lys Glu Leu Leu Glu Pro Met Leu Ala Val Gly
            500                 505                 510
Leu Ser Pro Ala Leu Thr Ala Val Leu Tyr Asp Leu Ser Arg Gln Ile
        515                 520                 525
Pro Gln Leu Lys Lys Asp Ile Gln Asp Gly Leu Leu Lys Met Leu Ser
    530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
                565                 570                 575
Ser Asp Val Gly Ser Ile Thr Leu Ala Leu Arg Thr Leu Gly Ser Phe
            580                 585                 590
Glu Phe Glu Gly His Ser Leu Thr Gln Phe Val Arg His Cys Ala Asp
        595                 600                 605
His Phe Leu Asn Ser Glu His Lys Glu Ile Arg Met Glu Ala Ala Arg
    610                 615                 620
Thr Cys Ser Arg Leu Leu Thr Pro Ser Ile His Leu Ile Ser Gly His
625                 630                 635                 640
Ala His Val Val Ser Gln Thr Ala Val Gln Val Val Ala Asp Val Leu
                645                 650                 655
Ser Lys Leu Leu Val Val Gly Ile Thr Asp Pro Asp Pro Asp Ile Arg
            660                 665                 670
Tyr Cys Val Leu Ala Ser Leu Asp Glu Arg Phe Asp Ala His Leu Ala
        675                 680                 685
Gln Ala Glu Asn Leu Gln Ala Leu Phe Val Ala Leu Asn Asp Gln Val
    690                 695                 700
Phe Glu Ile Arg Glu Leu Ala Ile Cys Thr Val Gly Arg Leu Ser Ser
705                 710                 715                 720
Met Asn Pro Ala Phe Val Met Pro Phe Leu Arg Lys Met Leu Ile Gln
                725                 730                 735
Ile Leu Thr Glu Leu Glu His Ser Gly Ile Gly Arg Ile Lys Glu Gln
            740                 745                 750
Ser Ala Arg Met Leu Gly His Leu Val Ser Asn Ala Pro Arg Leu Ile
        755                 760                 765
Arg Pro Tyr Met Glu Pro Ile Leu Lys Ala Leu Ile Leu Lys Leu Lys
    770                 775                 780
Asp Pro Asp Pro Asp Pro Asn Pro Gly Val Ile Asn Asn Val Leu Ala
785                 790                 795                 800
Thr Ile Gly Glu Leu Ala Gln Val Ser Gly Leu Glu Met Arg Lys Trp
                805                 810                 815
Val Asp Glu Leu Phe Ile Ile Ile Met Asp Met Leu Gln Asp Ser Ser
            820                 825                 830
Leu Leu Ala Lys Arg Gln Val Ala Leu Trp Thr Leu Gly Gln Leu Val
```

```
                835                 840                 845
Ala Ser Thr Gly Tyr Val Val Glu Pro Tyr Arg Lys Tyr Pro Thr Leu
        850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
        900                 905                 910

Ser Ala Val Ser Leu Ser Glu Ser Lys Ser Ser Gln Asp Ser Ser Asp
                915                 920                 925

Tyr Ser Thr Ser Glu Met Leu Val Asn Met Gly Asn Leu Pro Leu Asp
        930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
                965                 970                 975

Phe Ile Phe Lys Ser Leu Gly Leu Lys Cys Val Gln Phe Leu Pro Gln
        980                 985                 990

Val Met Pro Thr Phe Leu Asn Val Ile Arg Val Cys Asp Gly Ala Ile
        995                 1000                1005

Arg Glu Phe Leu Phe Gln Gln Leu Gly Met Leu Val Ser Phe Val Lys
   1010                  1015                1020

Ser His Ile Arg Pro Tyr Met Asp Glu Ile Val Thr Leu Met Arg Glu
1025                 1030                1035                1040

Phe Trp Val Met Asn Thr Ser Ile Gln Ser Thr Ile Ile Leu Leu Ile
                1045                1050                1055

Glu Gln Ile Val Val Ala Leu Gly Gly Glu Phe Lys Leu Tyr Leu Pro
        1060                1065                1070

Gln Leu Ile Pro His Met Leu Arg Val Phe Met His Asp Asn Ser Pro
        1075                1080                1085

Gly Arg Ile Val Ser Ile Lys Leu Leu Ala Ala Ile Gln Leu Phe Gly
   1090                  1095                1100

Ala Asn Leu Asp Asp Tyr Leu His Leu Leu Pro Pro Ile Val Lys
1105                 1110                1115                1120

Leu Phe Asp Ala Pro Glu Ala Pro Leu Pro Ser Arg Lys Ala Ala Leu
                1125                1130                1135

Glu Thr Val Asp Arg Leu Thr Glu Ser Leu Asp Phe Thr Asp Tyr Ala
        1140                1145                1150

Ser Arg Ile Ile His Pro Ile Val Arg Thr Leu Asp Gln Ser Pro Glu
   1155                  1160                1165

Leu Arg Ser Thr Ala Met Asp Thr Leu Ser Ser Leu Val Phe Gln Leu
   1170                  1175                1180

Gly Lys Lys Tyr Gln Ile Phe Ile Pro Met Val Asn Lys Val Leu Val
1185                 1190                1195                1200

Arg His Arg Ile Asn His Gln Arg Tyr Asp Val Leu Ile Cys Arg Ile
                1205                1210                1215

Val Lys Gly Tyr Thr Leu Ala Asp Glu Glu Asp Pro Leu Ile Tyr
        1220                1225                1230

Gln His Arg Met Leu Arg Ser Gly Gln Gly Asp Ala Leu Ala Ser Gly
        1235                1240                1245

Pro Val Glu Thr Gly Pro Met Lys Lys Leu His Val Ser Thr Ile Asn
   1250                  1255                1260
```

-continued

Leu Gln Lys Ala Trp Gly Ala Ala Arg Arg Val Ser Lys Asp Asp Trp
1265                1270                1275                1280

Leu Glu Trp Leu Arg Arg Leu Ser Leu Glu Leu Leu Lys Asp Ser Ser
            1285                1290                1295

Ser Pro Ser Leu Arg Ser Cys Trp Ala Leu Ala Gln Ala Tyr Asn Pro
        1300                1305                1310

Met Ala Arg Asp Leu Phe Asn Ala Ala Phe Val Ser Cys Trp Ser Glu
        1315                1320                1325

Leu Asn Glu Asp Gln Gln Asp Glu Leu Ile Arg Ser Ile Glu Leu Ala
    1330                1335                1340

Leu Thr Ser Gln Asp Ile Ala Glu Val Thr Gln Thr Leu Leu Asn Leu
1345                1350                1355                1360

Ala Glu Phe Met Glu His Ser Asp Lys Gly Pro Leu Pro Leu Arg Asp
            1365                1370                1375

Asp Asn Gly Ile Val Leu Leu Gly Glu Arg Ala Ala Lys Cys Arg Ala
        1380                1385                1390

Tyr Ala Lys Ala Leu His Tyr Lys Glu Leu Glu Phe Gln Lys Gly Pro
        1395                1400                1405

Thr Pro Ala Ile Leu Glu Ser Leu Ile Ser Ile Asn Asn Lys Leu Gln
    1410                1415                1420

Gln Pro Glu Ala Ala Ala Gly Val Leu Glu Tyr Ala Met Lys His Phe
1425                1430                1435                1440

Gly Glu Leu Glu Ile Gln Ala Thr Trp Tyr Glu Lys Leu His Glu Trp
            1445                1450                1455

Glu Asp Ala Leu Val Ala Tyr Asp Lys Lys Met Asp Thr Asn Lys Asp
        1460                1465                1470

Asp Pro Glu Leu Met Leu Gly Arg Met Arg Cys Leu Glu Ala Leu Gly
    1475                1480                1485

Glu Trp Gly Gln Leu His Gln Gln Cys Cys Glu Lys Trp Thr Leu Val
1490                1495                1500

Asn Asp Glu Thr Gln Ala Lys Met Ala Arg Met Ala Ala Ala Ala Ala
1505                1510                1515                1520

Trp Gly Leu Gly Gln Trp Asp Ser Met Glu Glu Tyr Thr Cys Met Ile
            1525                1530                1535

Pro Arg Asp Thr His Asp Gly Ala Phe Tyr Arg Ala Val Leu Ala Leu
        1540                1545                1550

His Gln Asp Leu Phe Ser Leu Ala Gln Gln Cys Ile Asp Lys Ala Arg
    1555                1560                1565

Asp Leu Leu Asp Ala Glu Leu Thr Ala Met Ala Gly Glu Ser Tyr Ser
    1570                1575                1580

Arg Ala Tyr Gly Ala Met Val Ser Cys His Met Leu Ser Glu Leu Glu
1585                1590                1595                1600

Glu Val Ile Gln Tyr Lys Leu Val Pro Glu Arg Arg Glu Ile Ile Arg
            1605                1610                1615

Gln Ile Trp Trp Glu Arg Leu Gln Gly Cys Gln Arg Ile Val Glu Asp
        1620                1625                1630

Trp Gln Lys Ile Leu Met Val Arg Ser Leu Val Val Ser Pro His Glu
    1635                1640                1645

Asp Met Arg Thr Trp Leu Lys Tyr Ala Ser Leu Cys Gly Lys Ser Gly
    1650                1655                1660

Arg Leu Ala Leu Ala His Lys Thr Leu Val Leu Leu Leu Gly Val Asp
1665                1670                1675                1680

Pro Ser Arg Gln Leu Asp His Pro Leu Pro Thr Val His Pro Gln Val
            1685                1690                1695

-continued

```
Thr Tyr Ala Tyr Met Lys Asn Met Trp Lys Ser Ala Arg Lys Ile Asp
        1700                1705                1710
Ala Phe Gln His Met Gln His Phe Val Gln Thr Met Gln Gln Gln Ala
    1715                1720                1725
Gln His Ala Ile Ala Thr Glu Asp Gln Gln His Lys Gln Glu Leu His
1730                1735                1740
Lys Leu Met Ala Arg Cys Phe Leu Lys Leu Gly Glu Trp Gln Leu Asn
1745                1750                1755                1760
Leu Gln Gly Ile Asn Glu Ser Thr Ile Pro Lys Val Leu Gln Tyr Tyr
                1765                1770                1775
Ser Ala Ala Thr Glu His Asp Arg Ser Trp Tyr Lys Ala Trp His Ala
            1780                1785                1790
Trp Ala Val Met Asn Phe Glu Ala Val Leu His Tyr Lys His Gln Asn
        1795                1800                1805
Gln Ala Arg Asp Glu Lys Lys Lys Leu Arg His Ala Ser Gly Ala Asn
    1810                1815                1820
Ile Thr Asn Ala Thr Thr Ala Ala Thr Thr Ala Ala Thr Ala Thr Thr
1825                1830                1835                1840
Thr Ala Ser Thr Glu Gly Ser Asn Ser Glu Ser Glu Ala Glu Ser Thr
                1845                1850                1855
Glu Asn Ser Pro Thr Pro Ser Pro Leu Gln Lys Lys Val Thr Glu Asp
        1860                1865                1870
Leu Ser Lys Thr Leu Leu Met Tyr Thr Val Pro Ala Val Gln Gly Phe
            1875                1880                1885
Phe Arg Ser Ile Ser Leu Ser Arg Gly Asn Asn Leu Gln Asp Thr Leu
        1890                1895                1900
Arg Val Leu Thr Leu Trp Phe Asp Tyr Gly His Trp Pro Asp Val Asn
1905                1910                1915                1920
Glu Ala Leu Val Glu Gly Val Lys Ala Ile Gln Ile Asp Thr Trp Leu
                1925                1930                1935
Gln Val Ile Pro Gln Leu Ile Ala Arg Ile Asp Thr Pro Arg Pro Leu
    1940                1945                1950
Val Gly Arg Leu Ile His Gln Leu Leu Thr Asp Ile Gly Arg Tyr His
        1955                1960                1965
Pro Gln Ala Leu Ile Tyr Pro Leu Thr Val Ala Ser Lys Ser Thr Thr
    1970                1975                1980
Thr Ala Arg His Asn Ala Ala Asn Lys Ile Leu Lys Asn Met Cys Glu
1985                1990                1995                2000
His Ser Asn Thr Leu Val Gln Gln Ala Met Met Val Ser Glu Glu Leu
                2005                2010                2015
Ile Arg Val Ala Ile Leu Trp His Glu Met Trp His Glu Gly Leu Glu
            2020                2025                2030
Glu Ala Ser Arg Leu Tyr Phe Gly Glu Arg Asn Val Lys Gly Met Phe
        2035                2040                2045
Glu Val Leu Glu Pro Leu His Ala Met Met Glu Arg Gly Pro Gln Thr
    2050                2055                2060
Leu Lys Glu Thr Ser Phe Asn Gln Ala Tyr Gly Arg Asp Leu Met Glu
2065                2070                2075                2080
Ala Gln Glu Trp Cys Arg Lys Tyr Met Lys Ser Gly Asn Val Lys Asp
                2085                2090                2095
Leu Thr Gln Ala Trp Asp Leu Tyr Tyr His Val Phe Arg Arg Ile Ser
            2100                2105                2110
Lys Gln Leu Pro Gln Leu Thr Ser Leu Glu Leu Gln Tyr Val Ser Pro
```

-continued

```
            2115                2120                2125
Lys Leu Leu Met Cys Arg Asp Leu Glu Leu Ala Val Pro Gly Thr Tyr
        2130                2135                2140
Asp Pro Asn Gln Pro Ile Ile Arg Ile Gln Ser Ile Ala Pro Ser Leu
2145                2150                2155                2160
Gln Val Ile Thr Ser Lys Gln Arg Pro Arg Lys Leu Thr Leu Met Gly
            2165                2170                2175
Ser Asn Gly His Glu Phe Val Phe Leu Leu Lys Gly His Glu Asp Leu
        2180                2185                2190
Arg Gln Asp Glu Arg Val Met Gln Leu Phe Gly Leu Val Asn Thr Leu
        2195                2200                2205
Leu Ala Asn Asp Pro Thr Ser Leu Arg Lys Asn Leu Ser Ile Gln Arg
        2210                2215                2220
Tyr Ala Val Ile Pro Leu Ser Thr Asn Ser Gly Leu Ile Gly Trp Val
2225                2230                2235                2240
Pro His Cys Asp Thr Leu His Ala Leu Ile Arg Asp Tyr Arg Glu Lys
            2245                2250                2255
Lys Lys Ile Leu Leu Asn Ile Glu His Arg Ile Met Leu Arg Met Ala
        2260                2265                2270
Pro Asp Tyr Asp His Leu Thr Leu Met Gln Lys Val Glu Val Phe Glu
        2275                2280                2285
His Ala Val Asn Asn Thr Ala Gly Asp Asp Leu Ala Lys Leu Leu Trp
        2290                2295                2300
Leu Lys Ser Pro Ser Ser Glu Val Trp Phe Asp Arg Arg Thr Asn Tyr
2305                2310                2315                2320
Thr Arg Ser Leu Ala Val Met Ser Met Val Gly Tyr Ile Leu Gly Leu
            2325                2330                2335
Gly Asp Arg His Pro Ser Asn Leu Met Leu Asp Arg Leu Ser Gly Lys
        2340                2345                2350
Ile Leu His Ile Asp Phe Gly Asp Cys Phe Glu Val Ala Met Thr Arg
        2355                2360                2365
Glu Lys Phe Pro Glu Lys Ile Pro Phe Arg Leu Thr Arg Met Leu Thr
        2370                2375                2380
Asn Ala Met Glu Val Thr Gly Leu Asp Gly Asn Tyr Arg Ile Thr Cys
2385                2390                2395                2400
His Thr Val Met Glu Val Leu Arg Glu His Lys Asp Ser Val Met Ala
            2405                2410                2415
Val Leu Glu Ala Phe Val Tyr Asp Pro Leu Leu Asn Trp Arg Leu Met
        2420                2425                2430
Asp Thr Asn Thr Lys Gly Asn Lys Arg Ser Arg Thr Arg Thr Asp Ser
        2435                2440                2445
Tyr Ser Ala Gly Gln Ser Val Glu Ile Leu Asp Gly Val Glu Leu Gly
        2450                2455                2460
Glu Pro Ala His Lys Lys Thr Gly Thr Thr Val Pro Glu Ser Ile His
2465                2470                2475                2480
Ser Phe Ile Gly Asp Gly Leu Val Lys Pro Glu Ala Leu Asn Lys Lys
            2485                2490                2495
Ala Ile Gln Ile Ile Asn Arg Val Arg Asp Lys Leu Thr Gly Arg Asp
        2500                2505                2510
Phe Ser His Asp Asp Thr Leu Asp Val Pro Thr Gln Val Glu Leu Leu
        2515                2520                2525
Ile Lys Gln Ala Thr Ser His Glu Asn Leu Cys Gln Cys Tyr Ile Gly
        2530                2535                2540
```

```
Trp Cys Pro Phe Trp
                2545

<210> SEQ ID NO 2
<211> LENGTH: 1036
<212> TYPE: PRT
<213> ORGANISM: Artificial Sequence
<220> FEATURE:
<223> OTHER INFORMATION: Amino acid sequence of phospholipase D1
      [Rattus norvegicus]
<220> FEATURE:
<221> NAME/KEY: misc_feature
<222> LOCATION: (719)..(719)
<223> OTHER INFORMATION: Xaa can be any naturally occurring amino acid

<400> SEQUENCE: 2

Met Ser Leu Arg Ser Glu Ala Arg Val Asn Thr Ser Thr Leu Gln Lys
 1               5                  10                  15

Ile Ala Ala Asp Met Arg Asn Leu Ile Glu Asn Leu Asp Thr Arg Glu
             20                  25                  30

Leu His Phe Glu Gly Glu Val Glu Tyr Asp Ala Ser Pro Gly Asp
         35                  40                  45

Pro Thr Ala Gln Glu Ala Cys Ile Pro Phe Ser Ser Ile Tyr Asn Thr
     50                  55                  60

Gln Gly Phe Lys Glu Pro Asn Ile Gln Ile Tyr Leu Ser Gly Cys Pro
 65                  70                  75                  80

Val Lys Ala Gln Val Leu Glu Val Glu Arg Phe Thr Ser Thr Ser Arg
                 85                  90                  95

Met Pro Ser Val Asn Leu Tyr Thr Ile Glu Leu Thr His Gly Glu Phe
            100                 105                 110

Thr Trp Gln Val Lys Arg Lys Phe Lys His Phe Gln Glu Phe His Arg
        115                 120                 125

Glu Leu Leu Lys Tyr Lys Ala Phe Ile Arg Ile Pro Ile Pro Thr Lys
    130                 135                 140

Arg His Thr Phe Arg Arg Gln Asn Val Lys Glu Glu Pro Arg Glu Met
145                 150                 155                 160

Pro Ser Leu Pro Arg Ser Ser Glu Asn Ala Ile Gln Glu Glu Gln Phe
                165                 170                 175

Phe Gly Arg Arg Lys Gln Leu Glu Asp Tyr Leu Thr Lys Ile Leu Lys
            180                 185                 190

Met Pro Met Tyr Arg Asn Tyr His Ala Thr Thr Glu Phe Leu Asp Val
        195                 200                 205

Ser Gln Leu Ser Phe Ile His Asp Leu Gly Pro Lys Gly Leu Glu Gly
    210                 215                 220

Met Ile Met Lys Arg Ser Gly Gly His Arg Ile Pro Gly Val Asn Cys
225                 230                 235                 240

Cys Gly His Gly Arg Ala Cys Tyr Arg Trp Ser Lys Arg Trp Leu Ile
                245                 250                 255

Val Lys Asp Ser Phe Leu Leu Tyr Met Lys Pro Asp Ser Gly Ala Ile
            260                 265                 270

Ala Phe Val Leu Leu Val Asp Lys Glu Phe Arg Ile Lys Val Gly Lys
        275                 280                 285

Lys Glu Thr Glu Thr Lys Tyr Gly Leu Arg Ile Asp Asn Leu Ser Arg
    290                 295                 300

Thr Leu Ile Leu Lys Cys Asn Ser Tyr Arg His Ala Arg Trp Trp Gly
305                 310                 315                 320

Gly Ala Ile Glu Glu Phe Ile Gln Lys His Gly Thr Asp Phe Leu Lys
                325                 330                 335
```

```
Asp His Arg Phe Gly Ser Tyr Ala Ala Val His Glu Asn Ile Leu Ala
            340                 345                 350

Lys Trp Tyr Val Asn Ala Lys Gly Tyr Phe Glu Asp Ile Ala Asn Ala
        355                 360                 365

Met Glu Gly Ala Thr Glu Ile Phe Ile Thr Asp Trp Trp Leu Ser
370                 375                 380

Pro Glu Ile Phe Leu Lys Arg Pro Val Glu Gly Asn Arg Trp Arg
385                 390                 395                 400

Leu Asp Cys Ile Leu Lys Arg Lys Ala Gln Gln Gly Val Arg Ile Phe
                405                 410                 415

Ile Met Leu Tyr Lys Glu Val Glu Leu Ala Leu Gly Ile Asn Ser Glu
            420                 425                 430

Tyr Thr Lys Arg Thr Leu Met Arg Leu His Pro Asn Ile Lys Val Met
        435                 440                 445

Arg His Pro Asp His Val Ser Ser Val Tyr Leu Trp Ala His His
450                 455                 460

Glu Lys Leu Val Ile Ile Asp Gln Ser Val Ala Phe Val Gly Gly Ile
465                 470                 475                 480

Asp Leu Ala Tyr Gly Arg Trp Asp Asp Asn Glu His Arg Leu Thr Asp
                485                 490                 495

Val Gly Ser Val Lys Arg Val Thr Ser Gly Gln Ser Leu Gly Ser Leu
            500                 505                 510

Thr Ala Ala Ser Val Glu Ser Met Glu Ser Leu Ser Leu Lys Asp Lys
        515                 520                 525

His Gln Ser His Lys Asn Glu Pro Val Leu Lys Ser Val Asn Asp Thr
530                 535                 540

Asp Met Lys Leu Lys Gly Ile Gly Lys Ser Arg Lys Phe Ser Lys Phe
545                 550                 555                 560

Ser Leu Tyr Arg Gln Leu His Arg Arg Asn Leu His Asn Ser Asp Ser
                565                 570                 575

Ile Ser Ser Val Asp Ser Ala Ser Asn Thr Gly Ser Ile Arg Ser Val
            580                 585                 590

Gln Thr Gly Val Gly Glu Leu His Gly Glu Thr Arg Phe Trp His Gly
        595                 600                 605

Lys Asp Tyr Cys Asn Phe Val Phe Lys Asp Trp Val Gln Leu Asp Lys
610                 615                 620

Pro Phe Ala Asp Phe Ile Asp Arg Tyr Ser Thr Pro Arg Met Pro Trp
625                 630                 635                 640

His Asp Ile Gly Ser Val Val His Gly Lys Ala Ala Arg Asp Val Ala
                645                 650                 655

Arg His Phe Ile Gln Arg Trp Asn Phe Thr Lys Ile Met Lys Pro Lys
            660                 665                 670

Tyr Arg Ser Leu Ser Tyr Pro Phe Leu Leu Pro Lys Ser Gln Ala Thr
        675                 680                 685

Ala His Glu Leu Arg Tyr Gln Val Pro Gly Ala Val His Ala Lys Ala
690                 695                 700

Gln Leu Leu Arg Ser Ala Ala Asp Trp Ser Ala Gly Ile Lys Xaa His
705                 710                 715                 720

Glu Glu Ser Ile His Ala Ala Tyr Thr His Val Ile Glu Asn Ser Lys
                725                 730                 735

His Tyr Ile Tyr Ile Glu Asn Gln Phe Phe Ile Ser Cys Ala Asp Asp
            740                 745                 750

Lys Val Val Phe Asn Lys Val Gly Asn Ala Ile Ala Gln Arg Ile Leu
```

```
                755                 760                 765
Lys Ala His Arg Glu Gly Gln Arg Tyr Arg Val Tyr Ile Val Ile Pro
    770                 775                 780

Leu Leu Pro Gly Phe Glu Gly Asp Ile Ser Thr Gly Gly Asn Ala
785                 790                 795                 800

Leu Gln Ala Ile Met His Phe Asn Tyr Arg Thr Met Cys Arg Gly Glu
                    805                 810                 815

Ser Ser Ile Leu Glu Gln Leu Lys Pro Glu Leu Gly Asn Lys Trp Ile
                820                 825                 830

Asn Tyr Ile Ser Phe Cys Gly Leu Arg Thr His Ala Glu Leu Glu Gly
                835                 840                 845

Asn Leu Val Thr Glu Leu Ile Tyr Val His Ser Lys Leu Leu Ile Ala
850                 855                 860

Asp Asp Asn Thr Val Ile Ile Gly Ser Ala Asn Ile Asn Asp Arg Ser
865                 870                 875                 880

Met Leu Gly Lys Arg Asp Ser Glu Met Ala Val Ile Val Gln Asp Arg
                    885                 890                 895

Gln Thr Val Pro Ser Val Met Asp Gly Lys Glu Tyr Gln Ala Gly Arg
                900                 905                 910

Phe Ala Gln Gly Leu Arg Leu Glu Cys Phe Arg Leu Val Leu Gly Tyr
                915                 920                 925

Leu Ser Asp Pro Ser Glu Asp Ile Gln Asp Pro Val Ser Asp Lys Phe
                930                 935                 940

Phe Lys Glu Ile Trp Val Ser Thr Ala Ala Arg Asn Ala Thr Ile Tyr
945                 950                 955                 960

Asp Lys Val Phe Arg Cys Leu Pro Asn Asp Glu Val His Asn Leu Ile
                    965                 970                 975

Gln Leu Arg Asp Phe Ile Asn Lys Pro Ile Leu Ala Lys Glu Asp Arg
                980                 985                 990

Leu Arg Ala Glu Glu Leu Arg  Lys Ile Arg Gly Phe  Leu Val Gln
                995                 1000                1005

Phe Pro  Phe Tyr Phe Leu Ser  Glu Glu Asn Leu Leu  Pro Ser Val
    1010                1015                1020

Gly Thr  Lys Glu Ala Ile Val  Pro Met Glu Val Trp  Thr
    1025                1030                1035

<210> SEQ ID NO 3
<211> LENGTH: 933
<212> TYPE: PRT
<213> ORGANISM: Artificial Sequence
<220> FEATURE:
<223> OTHER INFORMATION: Amino acid sequence of phospholipase D2 [Homo
      sapiens]

<400> SEQUENCE: 3

Met Thr Ala Thr Pro Glu Ser Leu Phe Pro Thr Gly Asp Glu Leu Asp
  1               5                  10                  15

Ser Ser Gln Leu Gln Met Glu Ser Asp Glu Val Asp Thr Leu Lys Glu
                 20                  25                  30

Gly Glu Asp Pro Ala Asp Arg Met His Pro Phe Leu Ala Ile Tyr Glu
             35                  40                  45

Leu Gln Ser Leu Lys Val His Pro Leu Val Phe Ala Pro Gly Val Pro
         50                  55                  60

Val Thr Ala Gln Val Val Gly Thr Glu Arg Tyr Thr Ser Gly Ser Lys
 65                  70                  75                  80

Val Gly Thr Cys Thr Leu Tyr Ser Val Arg Leu Thr His Gly Asp Phe
```

```
                     85                  90                  95
Ser Trp Thr Thr Lys Lys Tyr Arg His Phe Gln Glu Leu His Arg
                100                 105                 110

Asp Leu Leu Arg His Lys Val Leu Met Ser Leu Leu Pro Leu Ala Arg
                115                 120                 125

Phe Ala Val Ala Tyr Ser Pro Ala Arg Asp Ala Gly Asn Arg Glu Met
                130                 135                 140

Pro Ser Leu Pro Arg Ala Gly Pro Glu Gly Ser Thr Arg His Ala Ala
145                 150                 155                 160

Ser Lys Gln Lys Tyr Leu Glu Asn Tyr Leu Asn Cys Leu Leu Thr Met
                165                 170                 175

Ser Phe Tyr Arg Asn Tyr His Ala Met Thr Glu Phe Leu Glu Val Ser
                180                 185                 190

Gln Leu Ser Phe Ile Pro Asp Leu Gly Arg Lys Gly Leu Glu Gly Met
                195                 200                 205

Ile Arg Lys Arg Ser Gly Gly His Arg Val Pro Gly Leu Thr Cys Cys
                210                 215                 220

Gly Arg Asp Gln Val Cys Tyr Arg Trp Ser Lys Arg Trp Leu Val Val
225                 230                 235                 240

Lys Asp Ser Phe Leu Leu Tyr Met Cys Leu Glu Thr Gly Ala Ile Ser
                245                 250                 255

Phe Val Gln Leu Phe Asp Pro Gly Phe Glu Val Gln Val Gly Lys Arg
                260                 265                 270

Ser Thr Glu Ala Arg His Gly Val Arg Ile Asp Thr Ser His Arg Ser
                275                 280                 285

Leu Ile Leu Lys Cys Ser Ser Tyr Arg Gln Ala Arg Trp Trp Ala Gln
                290                 295                 300

Glu Ile Thr Glu Leu Ala Gln Gly Pro Gly Arg Asp Phe Leu Gln Leu
305                 310                 315                 320

His Arg His Asp Ser Tyr Ala Pro Pro Arg Pro Gly Thr Leu Ala Arg
                325                 330                 335

Trp Phe Val Asn Gly Ala Gly Tyr Phe Ala Ala Val Ala Asp Ala Ile
                340                 345                 350

Leu Arg Ala Gln Glu Glu Ile Phe Ile Thr Asp Trp Trp Leu Ser Pro
                355                 360                 365

Glu Val Tyr Leu Lys Arg Pro Ala His Ser Asp Asp Trp Arg Leu Asp
                370                 375                 380

Ile Met Leu Lys Arg Lys Ala Glu Glu Gly Val Arg Val Ser Ile Leu
385                 390                 395                 400

Leu Phe Lys Glu Val Glu Leu Ala Leu Gly Ile Asn Ser Gly Tyr Ser
                405                 410                 415

Lys Arg Ala Leu Met Leu Leu His Pro Asn Ile Lys Val Met Arg His
                420                 425                 430

Pro Asp Gln Val Thr Leu Trp Ala His His Glu Lys Leu Leu Val Val
                435                 440                 445

Asp Gln Val Val Ala Phe Leu Gly Gly Leu Asp Leu Ala Tyr Gly Arg
                450                 455                 460

Trp Asp Asp Leu His Tyr Arg Leu Thr Asp Leu Gly Asp Ser Ser Glu
465                 470                 475                 480

Ser Ala Ala Ser Gln Pro Pro Thr Pro Arg Pro Asp Ser Pro Ala Thr
                485                 490                 495

Pro Asp Leu Ser His Asn Gln Phe Phe Trp Leu Gly Lys Asp Tyr Ser
                500                 505                 510
```

```
Asn Leu Ile Thr Lys Asp Trp Val Gln Leu Asp Arg Pro Phe Glu Asp
    515                 520                 525

Phe Ile Asp Arg Glu Thr Thr Pro Arg Met Pro Trp Arg Asp Val Gly
530                 535                 540

Val Val Val His Gly Leu Pro Ala Arg Asp Leu Ala Arg His Phe Ile
545                 550                 555                 560

Gln Arg Trp Asn Phe Thr Lys Thr Thr Lys Ala Lys Tyr Lys Thr Pro
                565                 570                 575

Ile Tyr Pro Tyr Leu Leu Pro Lys Ser Thr Ser Thr Ala Asn Gln Leu
                580                 585                 590

Pro Phe Thr Leu Pro Gly Gly Gln Cys Thr Thr Val Gln Val Leu Arg
            595                 600                 605

Ser Val Asp Arg Trp Ser Ala Gly Thr Leu Glu Asn Ser Ile Leu Asn
        610                 615                 620

Ala Tyr Leu His Thr Ile Arg Glu Ser Gln His Phe Leu Tyr Ile Glu
625                 630                 635                 640

Asn Gln Phe Phe Ile Ser Cys Ser Asp Gly Arg Thr Val Leu Asn Lys
                645                 650                 655

Val Gly Asp Glu Ile Val Asp Arg Ile Leu Lys Ala His Lys Gln Gly
            660                 665                 670

Trp Cys Tyr Arg Val Tyr Val Leu Leu Pro Leu Leu Pro Gly Phe Glu
        675                 680                 685

Gly Asp Ile Ser Thr Gly Gly Gly Asn Ser Ile Gln Ala Ile Leu His
690                 695                 700

Phe Thr Tyr Arg Thr Leu Cys Arg Gly Glu Tyr Ser Ile Leu His Arg
705                 710                 715                 720

Leu Lys Ala Ala Met Gly Thr Ala Trp Arg Asp Tyr Ile Ser Ile Cys
                725                 730                 735

Gly Leu Arg Thr His Gly Glu Leu Gly Gly His Pro Val Ser Glu Leu
            740                 745                 750

Ile Tyr Ile His Ser Lys Val Leu Ile Ala Asp Asp Arg Thr Val Ile
        755                 760                 765

Ile Gly Ser Ala Asn Ile Asn Asp Arg Ser Leu Leu Gly Lys Arg Asp
770                 775                 780

Ser Glu Leu Ala Val Leu Ile Glu Asp Thr Glu Thr Glu Pro Ser Leu
785                 790                 795                 800

Met Asn Gly Ala Glu Tyr Gln Ala Gly Arg Phe Ala Leu Ser Leu Arg
                805                 810                 815

Lys His Cys Phe Gly Val Ile Leu Gly Ala Asn Thr Arg Pro Asp Leu
            820                 825                 830

Asp Leu Arg Asp Pro Ile Cys Asp Asp Phe Phe Gln Leu Trp Gln Asp
        835                 840                 845

Met Ala Glu Ser Asn Ala Asn Ile Tyr Glu Gln Ile Phe Arg Cys Leu
850                 855                 860

Pro Ser Asn Ala Thr Arg Ser Leu Arg Thr Leu Arg Glu Tyr Val Ala
865                 870                 875                 880

Val Glu Pro Leu Ala Thr Val Ser Pro Pro Leu Ala Arg Ser Glu Leu
                885                 890                 895

Thr Gln Val Gln Gly His Leu Val His Phe Pro Leu Lys Phe Leu Glu
            900                 905                 910

Asp Glu Ser Leu Leu Pro Pro Leu Gly Ser Lys Glu Gly Met Ile Pro
        915                 920                 925

Leu Glu Val Trp Thr
    930
```

```
<210> SEQ ID NO 4
<211> LENGTH: 5
<212> TYPE: PRT
<213> ORGANISM: Artificial Sequence
<220> FEATURE:
<223> OTHER INFORMATION: Amino acid sequence of 165-169 of phospholipase
      D2 [Homos apiens]

<400> SEQUENCE: 4

Phe Glu Val Gln Val
 1               5

<210> SEQ ID NO 5
<211> LENGTH: 1335
<212> TYPE: PRT
<213> ORGANISM: Artificial Sequence
<220> FEATURE:
<223> OTHER INFORMATION: Amino acid sequence of regulatory-associated
      protein of mTOR (Raptor) (P150 target of rapamycin (TOR)-scaffold
      protein) [Homo sapiens]

<400> SEQUENCE: 5

Met Glu Ser Glu Met Leu Gln Ser Pro Leu Leu Gly Leu Gly Glu Glu
 1               5                  10                  15

Asp Glu Ala Asp Leu Thr Asp Trp Asn Leu Pro Leu Ala Phe Met Lys
             20                  25                  30

Lys Arg His Cys Glu Lys Ile Glu Gly Ser Lys Ser Leu Ala Gln Ser
         35                  40                  45

Trp Arg Met Lys Asp Arg Met Lys Thr Val Ser Val Ala Leu Val Leu
     50                  55                  60

Cys Leu Asn Val Gly Val Asp Pro Pro Asp Val Val Lys Thr Thr Pro
 65                  70                  75                  80

Cys Ala Arg Leu Glu Cys Trp Ile Asp Pro Leu Ser Met Gly Pro Gln
                 85                  90                  95

Lys Ala Leu Glu Thr Ile Gly Ala Asn Leu Gln Lys Gln Tyr Glu Asn
            100                 105                 110

Trp Gln Pro Arg Ala Arg Tyr Lys Gln Ser Leu Asp Pro Thr Val Asp
        115                 120                 125

Glu Val Lys Lys Leu Cys Thr Ser Leu Arg Arg Asn Ala Lys Glu Glu
    130                 135                 140

Arg Val Leu Phe His Tyr Asn Gly His Gly Val Pro Arg Pro Thr Val
145                 150                 155                 160

Asn Gly Glu Val Trp Val Phe Asn Lys Asn Tyr Thr Gln Tyr Ile Pro
                165                 170                 175

Leu Ser Ile Tyr Asp Leu Gln Thr Trp Met Gly Ser Pro Ser Ile Phe
            180                 185                 190

Val Tyr Asp Cys Ser Asn Ala Gly Leu Ile Val Lys Ser Phe Lys Gln
        195                 200                 205

Phe Ala Leu Gln Arg Glu Gln Glu Leu Glu Val Ala Ala Ile Asn Pro
    210                 215                 220

Asn His Pro Leu Ala Gln Met Pro Leu Pro Ser Met Lys Asn Cys
225                 230                 235                 240

Ile Gln Leu Ala Ala Cys Glu Ala Thr Glu Leu Leu Pro Met Ile Pro
                245                 250                 255

Asp Leu Pro Ala Asp Leu Phe Thr Ser Cys Leu Thr Thr Pro Ile Lys
            260                 265                 270

Ile Ala Leu Arg Trp Phe Cys Met Gln Lys Cys Val Ser Leu Val Pro
        275                 280                 285
```

-continued

```
Gly Val Thr Leu Asp Leu Ile Glu Lys Ile Pro Gly Arg Leu Asn Asp
    290                 295                 300

Arg Arg Thr Pro Leu Gly Glu Leu Asn Trp Ile Phe Thr Ala Ile Thr
305                 310                 315                 320

Asp Thr Ile Ala Trp Asn Val Leu Pro Arg Asp Leu Phe Gln Lys Leu
                325                 330                 335

Phe Arg Gln Asp Leu Leu Val Ala Ser Leu Phe Arg Asn Phe Leu Leu
            340                 345                 350

Ala Glu Arg Ile Met Arg Ser Tyr Asn Cys Thr Pro Val Ser Ser Pro
        355                 360                 365

Arg Leu Pro Pro Thr Tyr Met His Ala Met Trp Gln Ala Trp Asp Leu
370                 375                 380

Ala Val Asp Ile Cys Leu Ser Gln Leu Pro Thr Ile Ile Glu Glu Gly
385                 390                 395                 400

Thr Ala Phe Arg His Ser Pro Phe Phe Ala Glu Gln Leu Thr Ala Phe
                405                 410                 415

Gln Val Trp Leu Thr Met Gly Val Glu Asn Arg Asn Pro Pro Glu Gln
            420                 425                 430

Leu Pro Ile Val Leu Gln Val Leu Leu Ser Gln Val His Arg Leu Arg
        435                 440                 445

Ala Leu Asp Leu Leu Gly Arg Phe Leu Asp Leu Gly Pro Trp Ala Val
450                 455                 460

Ser Leu Ala Leu Ser Val Gly Ile Phe Pro Tyr Val Leu Lys Leu Leu
465                 470                 475                 480

Gln Ser Ser Ala Arg Glu Leu Arg Pro Leu Leu Val Phe Ile Trp Ala
                485                 490                 495

Lys Ile Leu Ala Val Asp Ser Ser Cys Gln Ala Asp Leu Val Lys Asp
            500                 505                 510

Asn Gly His Lys Tyr Phe Leu Ser Val Leu Ala Asp Pro Tyr Met Pro
        515                 520                 525

Ala Glu His Arg Thr Met Thr Ala Phe Ile Leu Ala Val Ile Val Asn
530                 535                 540

Ser Tyr His Thr Gly Gln Glu Ala Cys Leu Gln Gly Asn Leu Ile Ala
545                 550                 555                 560

Ile Cys Leu Glu Gln Leu Asn Asp Pro His Pro Leu Leu Arg Gln Trp
                565                 570                 575

Val Ala Ile Cys Leu Gly Arg Ile Trp Gln Asn Phe Asp Ser Ala Arg
            580                 585                 590

Trp Cys Gly Val Arg Asp Ser Ala His Glu Lys Leu Tyr Ser Leu Leu
        595                 600                 605

Ser Asp Pro Ile Pro Glu Val Arg Cys Ala Ala Val Phe Ala Leu Gly
610                 615                 620

Thr Phe Val Gly Asn Ser Ala Glu Arg Thr Asp His Ser Thr Thr Ile
625                 630                 635                 640

Asp His Asn Val Ala Met Met Leu Ala Gln Leu Val Ser Asp Gly Ser
                645                 650                 655

Pro Met Val Arg Lys Glu Leu Val Val Ala Leu Ser His Leu Val Val
            660                 665                 670

Gln Tyr Glu Ser Asn Phe Cys Thr Val Ala Leu Gln Phe Ile Glu Glu
        675                 680                 685

Glu Lys Asn Tyr Ala Leu Pro Ser Pro Ala Thr Thr Glu Gly Gly Ser
690                 695                 700

Leu Thr Pro Val Arg Asp Ser Pro Cys Thr Pro Arg Leu Arg Ser Val
```

```
                705                 710                 715                 720
Ser Ser Tyr Gly Asn Ile Arg Ala Val Ala Thr Ala Arg Ser Leu Asn
                    725                 730                 735

Lys Ser Leu Gln Asn Leu Ser Leu Thr Glu Glu Ser Gly Gly Ala Val
                740                 745                 750

Ala Phe Ser Pro Gly Asn Leu Ser Thr Ser Ser Ala Ser Ser Thr
                755                 760                 765

Leu Gly Ser Pro Glu Asn Glu His Ile Leu Ser Phe Glu Thr Ile
    770                 775                 780

Asp Lys Met Arg Arg Ala Ser Ser Tyr Ser Ser Leu Asn Ser Leu Ile
785                 790                 795                 800

Gly Val Ser Phe Asn Ser Val Tyr Thr Gln Ile Trp Arg Val Leu Leu
                    805                 810                 815

His Leu Ala Ala Asp Pro Tyr Pro Glu Val Ser Asp Val Ala Met Lys
                    820                 825                 830

Val Leu Asn Ser Ile Ala Tyr Lys Ala Thr Val Asn Ala Arg Pro Gln
                835                 840                 845

Arg Val Leu Asp Thr Ser Ser Leu Thr Gln Ser Ala Pro Ala Ser Pro
    850                 855                 860

Thr Asn Lys Gly Val His Ile His Gln Ala Gly Gly Ser Pro Pro Ala
865                 870                 875                 880

Ser Ser Thr Ser Ser Ser Ser Leu Thr Asn Asp Val Ala Lys Gln Pro
                    885                 890                 895

Val Ser Arg Asp Leu Pro Ser Gly Arg Pro Gly Thr Thr Gly Pro Ala
                900                 905                 910

Gly Ala Gln Tyr Thr Pro His Ser His Gln Phe Pro Arg Thr Arg Lys
                915                 920                 925

Met Phe Asp Lys Gly Pro Glu Gln Thr Ala Asp Ala Asp Ala
                930                 935                 940

Ala Gly His Lys Ser Phe Ile Ser Ala Thr Val Gln Thr Gly Phe Cys
945                 950                 955                 960

Asp Trp Ser Ala Arg Tyr Phe Ala Gln Pro Val Met Lys Ile Pro Glu
                    965                 970                 975

Glu His Asp Leu Glu Ser Gln Ile Arg Lys Glu Arg Glu Trp Arg Phe
                980                 985                 990

Leu Arg Asn Ser Arg Val Arg Arg Gln Ala Gln Gln Val Ile Gln Lys
                995                 1000                1005

Gly Ile Thr Arg Leu Asp Asp Gln Ile Phe Leu Asn Arg Asn Pro Gly
    1010                1015                1020

Val Pro Ser Val Val Lys Phe His Pro Phe Thr Pro Cys Ile Ala Val
1025                1030                1035                1040

Ala Asp Lys Asp Ser Ile Cys Phe Trp Asp Trp Glu Lys Gly Glu Lys
                    1045                1050                1055

Leu Asp Tyr Phe His Asn Gly Asn Pro Arg Tyr Thr Arg Val Thr Ala
                1060                1065                1070

Met Glu Tyr Leu Asn Gly Gln Asp Cys Ser Leu Leu Leu Thr Ala Thr
    1075                1080                1085

Asp Asp Gly Ala Ile Arg Val Trp Lys Asn Phe Ala Asp Leu Glu Lys
    1090                1095                1100

Asn Pro Glu Met Val Thr Ala Trp Gln Gly Leu Ser Asp Met Leu Pro
1105                1110                1115                1120

Thr Thr Arg Gly Ala Gly Met Val Val Asp Trp Glu Gln Glu Thr Gly
                    1125                1130                1135
```

```
Leu Leu Met Ser Ser Gly Asp Val Arg Ile Val Arg Ile Trp Asp Thr
        1140                1145                1150

Asp Arg Glu Met Lys Val Gln Asp Ile Pro Thr Gly Ala Asp Ser Cys
    1155                1160                1165

Val Thr Ser Leu Ser Cys Asp Ser His Arg Ser Leu Ile Val Ala Gly
    1170                1175                1180

Leu Gly Asp Gly Ser Ile Arg Val Tyr Asp Arg Arg Met Ala Leu Ser
1185                1190                1195                1200

Glu Cys Arg Val Met Thr Tyr Arg Glu His Thr Ala Trp Val Val Lys
        1205                1210                1215

Ala Ser Leu Gln Lys Arg Pro Asp Gly His Ile Val Ser Val Ser Val
        1220                1225                1230

Asn Gly Asp Val Arg Ile Phe Asp Pro Arg Met Pro Glu Ser Val Asn
        1235                1240                1245

Val Leu Gln Ile Val Lys Gly Leu Thr Ala Leu Asp Ile His Pro Gln
        1250                1255                1260

Ala Asp Leu Ile Ala Cys Gly Ser Val Asn Gln Phe Thr Ala Ile Tyr
1265                1270                1275                1280

Asn Ser Ser Gly Glu Leu Ile Asn Asn Ile Lys Tyr Tyr Asp Gly Phe
        1285                1290                1295

Met Gly Gln Arg Val Gly Ala Ile Ser Cys Leu Ala Phe His Pro His
        1300                1305                1310

Trp Pro His Leu Ala Val Gly Ser Asn Asp Tyr Tyr Ile Ser Val Tyr
        1315                1320                1325

Ser Val Glu Lys Arg Val Arg
        1330                1335

<210> SEQ ID NO 6
<211> LENGTH: 24
<212> TYPE: DNA
<213> ORGANISM: Artificial Sequence
<220> FEATURE:
<223> OTHER INFORMATION: sense oligonucleotide for PCR of PLD2

<400> SEQUENCE: 6
ggccgagacc aagtttgtta tcgc                                          24

<210> SEQ ID NO 7
<211> LENGTH: 65
<212> TYPE: DNA
<213> ORGANISM: Artificial Sequence
<220> FEATURE:
<223> OTHER INFORMATION: antisense oligonucleotide (F265A)

<400> SEQUENCE: 7
ccatcgatcc gcacgccgtg ccgtgcctcc gtgctccttt tccccacttg cacctcagcg   60
ccagg                                                               65

<210> SEQ ID NO 8
<211> LENGTH: 65
<212> TYPE: DNA
<213> ORGANISM: Artificial Sequence
<220> FEATURE:
<223> OTHER INFORMATION: antisense oligonucleotide (E266R)

<400> SEQUENCE: 8
ccatcgatcc gcacgccgtg ccgtgcctcc gtgctccttt tccccacttg caccctaaag   60
ccagg                                                               65
```

```
<210> SEQ ID NO 9
<211> LENGTH: 21
<212> TYPE: RNA
<213> ORGANISM: Artificial Sequence
<220> FEATURE:
<223> OTHER INFORMATION: sense oligonucleotide corresponding to human
      PLD2 coding nucleotides 703-723

<400> SEQUENCE: 9
aagagguggc ugguggugaa g                                              21

<210> SEQ ID NO 10
<211> LENGTH: 21
<212> TYPE: RNA
<213> ORGANISM: Artificial Sequence
<220> FEATURE:
<223> OTHER INFORMATION: antisense oligonucleotide corresponding to
      human PLD2 coding nucleotides 703-723

<400> SEQUENCE: 10
cuucaccacc agccaccucu u                                              21

<210> SEQ ID NO 11
<211> LENGTH: 21
<212> TYPE: RNA
<213> ORGANISM: Artificial Sequence
<220> FEATURE:
<223> OTHER INFORMATION: sense oligonucleotide corresponding to human
      PLD1a coding nucleotides 1455-1475

<400> SEQUENCE: 11
aaggugggac gacaaugagc a                                              21

<210> SEQ ID NO 12
<211> LENGTH: 21
<212> TYPE: RNA
<213> ORGANISM: Artificial Sequence
<220> FEATURE:
<223> OTHER INFORMATION: antisense oligonucleotide corresponding to
      human PLD1a coding nucleotides 1455-1475

<400> SEQUENCE: 12
ugcucauugu cgucccaccu u                                              21

<210> SEQ ID NO 13
<211> LENGTH: 21
<212> TYPE: DNA
<213> ORGANISM: Artificial Sequence
<220> FEATURE:
<223> OTHER INFORMATION: nucleotides 703-723 of PLD2

<400> SEQUENCE: 13
aagaggtggc tggtggtgaa g                                              21
```